(12) United States Patent
Hayashi et al.

(10) Patent No.: US 7,575,892 B2
(45) Date of Patent: Aug. 18, 2009

(54) EXPRESSION VECTOR ENCODING A TRITERPENE HYDROXYLASE POLYPEPTIDE

(75) Inventors: Hiroaki Hayashi, Gifu (JP); Kenichiro Inoue, Osaka (JP); Masateru Hoshino, Bunkyo-ku (JP); Masaaki Shibuya, Bunkyo-ku (JP); Yutaka Ebizuka, Bunkyo-ku (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 49 days.

(21) Appl. No.: 10/590,661

(22) PCT Filed: Feb. 25, 2005

(86) PCT No.: PCT/JP2005/003205

§ 371 (c)(1),
(2), (4) Date: Aug. 25, 2006

(87) PCT Pub. No.: WO2005/080572

PCT Pub. Date: Sep. 1, 2005

(65) Prior Publication Data

US 2008/0003639 A1    Jan. 3, 2008

(30) Foreign Application Priority Data

Feb. 25, 2004    (JP)    .............................. 2004-049123

(51) Int. Cl.
| | |
|---|---|
| *C12P 33/06* | (2006.01) |
| *C12N 15/00* | (2006.01) |
| *C12N 1/20* | (2006.01) |
| *C12N 1/00* | (2006.01) |
| *C07H 21/04* | (2006.01) |
| *C12N 9/02* | (2006.01) |

(52) U.S. Cl. .................... 435/58; 435/189; 435/320.1; 435/69.1; 435/252.3; 435/254.11; 435/254.2; 536/23.2; 536/23.6

(58) Field of Classification Search ........................ None
See application file for complete search history.

(56) References Cited

U.S. PATENT DOCUMENTS

2004/0031072 A1 * 2/2004 La Rosa et al. ............. 800/278

FOREIGN PATENT DOCUMENTS

| | | | |
|---|---|---|---|
| JP | 61-37749 A | 2/1986 | |
| JP | 10-234396 A | 9/1998 | |
| WO | WO 02/086142 A | 10/2002 | |

OTHER PUBLICATIONS

Webster's online dictionary definition of "represent" obtained from www.merriam-webster.com/, last viewed on Apr. 2, 2008.*
Morita et al., Eur. J. Biochem., 267, 3543-3460, 2000.*
Branden et al., "Introduction to Protein Structure", Garland Publishing Inc., New York, 1991.*
Witkowski et al., Biochemistry 38:11643-11650, 1999.*
Dang et al., Clin Cancer Res 5:471-474, 1999.*
Fox, Nat Biotechnol 21:217, 2003.*
Juengst, BMJ 326:1410-1411, 2003.*
Shibuya et al., FEBS J. 273:948-959, 2006.*
Schopfer et al., FEBS Lett. 432:182-186, 1998.*
GenBank Accession No. AAA77063, Oct. 1995, 2 pages.*
Invitrogen pYES2 vector map, obtained from the internet web address tools.invitrogen.com/content/sfs/vectors/pyes2_map.pdf, last viewed on Nov. 3, 2008, 1 page.*
Isao Kitagawa et al., "Saponin and Sapogenol. XIII.[1)] Structures of Three Soybean Saponins: Soyasaponin I, Soyasaponin II, and Soyasaponin III" (1976), Chem. Pharm. Bull., vol. 24, pp. 121-129.
Isao Kitagawa et al., "Revised Structures of Soyasapogenols A, B, and E, Oleanene-Sapogenols from Soybean. Structures of Soyasaponins I, II, and III (1982), Chem. Pharm. Bull., vol. 30, pp. 2294-2297".
Kazue Sasaki et al., "Synthesis and Hepatoprotective Effects of Soyasapogenol B Derivatives" (1997), Bioorg. Med. Chem. Lett., vol. 7, No. 1, pp. 85-88.
Isao Kitagawa et al., "Characterization of Saponin Constituents in Soybeans of Various Origins and Quantitative Analysis of Soyasaponins by Gas-Liquid Chromatography" (1984), Yakugaku Zasshi, vol. 104, pp. 162-168.
Koichi Kimura et al., "Components of Sophora japonica L. II. On the Structure of Sophoradiol." (1958), Yakugaku Zasshi, vol. 78, pp. 1090-1094.

(Continued)

*Primary Examiner*—David J Steadman
(74) *Attorney, Agent, or Firm*—Sughrue Mion, PLLC

(57) ABSTRACT

Soyasapogenol B is biosynthesized via two steps of hydroxylation reaction of its precursor β-amyrin. However, the gene of the hydroxylase concerned in this reaction has not been revealed. Therefore, it was impossible to apply a genetic engineering technique on the hydroxylase. The present inventors reveals that a sequence which corresponds to a soybean-derived cytochrome P-450 gene CYP93E1 encodes an enzyme protein that carries out hydroxylation of the 24-position of an oleanane type triterpene, and also provides a method for applying said gene making use of a genetic engineering technique.

14 Claims, 7 Drawing Sheets

OTHER PUBLICATIONS

Christopher L. Steele et al., "Molecular Characterization of the Enzyme Catalyzing the Aryl Migration Reaction of Isoflavonoid Biosynthesis in Soybean", Archives of Biochemistry and Biophysics, vol. 367, No. 1, pp. 146-150, (Jul. 1, 1999).

Hiroaki Hayashi et al., "Glycyrrhetinic Acid 24-Hydroxylase Activity in Microsomes of Cultured Licorice Cells", Phytochemistry, vol. 34, No. 5, pp. 1303-1307, (1993).

* cited by examiner

EXPRESSION VECTOR ENCODING A TRITERPENE HYDROXYLASE POLYPEPTIDE

TECHNICAL FIELD

This invention relates to a cell transformed by a genetic engineering technique with an enzyme gene which is concerned in the biosynthesis of plant-derived soyasapogenol B, and a method for producing soyasapogenol B making use of the cell.

BACKGROUND OF THE INVENTION

Soyasapogenol B (12-oleanene-3,22,24-triol) is a triterpene having an oleanane skeleton, which has been isolated from a soybean seed and determined for its structure (*Chem. Pharm. Bull.*, 24, pp. 121-129, 1976, *Chem. Pharm. Bull.*, 30, pp. 2294-2297, 1982) (Non-patent References 1 and 2), and its glycoside soyasaponin is broadly distributed in leguminous plants.

Regarding the soyasapogenol B, its anti-complement activity and platelet agglutination inhibitory action (JP-A-61-37749) (Patent Reference 1), antitumor activity (JP-A-10-234396) (Patent Reference 2) and hepatoprotective activity (*Bioorg. Med. Chem. Lett.*, 7, 85-88, 1997) (Non-patent Reference 3) and the like have so far been reported, and its usefulness as a pharmaceutical preparation or a material thereof is expected.

Regarding the production method of soyasapogenol B, a method is known in which sugar chains of saponin contained in soybean seeds are hydrolyzed, and then soyasapogenol B is purified, but since the ratio of saponin contained in soybean seeds is about 0.2% which is very small (*Yakugaku Zasshi* (Journal of Pharmaceutical Sciences), 104, 162-168, 1984) (Non-patent Reference 4), more efficient production method is in demand.

It is considered that β-amyrin as a biosynthesis precursor of soyasapogenol B is biosynthesized by the ring-closure of 2,3-oxidosqualene which is formed via the mevalonate pathway, and soyasapogenol B is biosynthesized thereafter via two steps of hydroxylation reactions.

Sophoradiol (12-oleanene-3,22-diol) structurally close to soyasapogenol B is a substance which has been reported a component of *Kaika*(*Sophora japonica*) (*Yakugaku Zasshi*, 78, 1090-1094, 1958) (Non-patent Reference 5), and it is possible to produce soyasapogenol B by hydroxylation of the 24-position of sophoradiol.

Actually, a method for producing soyasapogenol B by hydroxylation of the 24-position of sophoradiol making use of a hydroxylase derived from a *Glycyrrhiza glabra* cultured cell has been disclosed (WO 02/086142) (Patent Reference 3).

Patent Reference 1: JP-A-61-37749
Patent Reference 2: JP-A-10-234396
Patent Reference 3: International Publication WO 02/086142
Non-patent Reference 1: *Chem. Pharm. Bull.*, 24, pp. 121-129, 1976
Non-patent Reference 2: *Chem. Pharm. Bull.*, 30, pp. 2294-2297, 1982
Non-patent Reference 3: *Bioorg. Med. Chem. Lett.*, 7, 85-88, 1997
Non-patent Reference 4: *Yakugaku Zasshi* (Journal of Pharmaceutical Sciences), 104, 162-168, 1984
Non-patent Reference 5: *Yakugaku Zasshi*, 78, 1090-1094, 1958

DISCLOSURE OF THE INVENTION

Problems that the Invention is to Solve

The β-amyrin is a biosynthetic precursor of soyasapogenol B. It is biosynthesized by the ring-closure of 2,3-oxidosqualene which is formed via the mevalonate pathway, and soyasapogenol B is biosynthesized thereafter via two steps of hydroxylation reaction. However, the gene of the hydroxylase concerned in this reaction has not been revealed. Therefore, it was impossible to apply a genetic engineering technique on the hydroxylase.

Means for Solving the Problems

Based on an assumption that the gene of a cytochrome P-450 type enzyme concerned in the biosynthesis of soyasapogenol B from β-amyrin is contained in an EST (Expression Sequence Tags) clone of soybean producing soyasaponin at a high production rate or in a clone whose function is unidentified, the present inventors have carried out analysis of functions of these soybean clones using a lanosterol deficient yeast mutant strain. Among the analyzed clones, the hydroxylation activity of the 24-position of an oleanane type triterpene, which cannot be detected originally, was detected in a yeast strain in which the polynucleotide represented by SEQ ID NO:8 was transcribed and translated. Polynucleotide sequence of the hydroxylation activity-detected enzyme is SEQ ID NO:8, and deduced polypeptide sequence is SEQ ID NO:9. As a sequence bearing resemblance to the SEQ ID NO:8, a cytochrome P-450 gene CYP93E1 (GenBank Accession Number AF135485, SEQ ID NO:10, deduced polypeptide sequence is SEQ ID NO:11) is known. The polynucleotide represented by SEQ ID NO:8 and the polynucleotide represented by SEQ ID NO:10 are different from each other in terms of 3 positions of the 121st position, the 171st position and the 1081st position (hereinafter, the sequence represented by SEQ ID NO:8 is also called cytochrome P-450 gene CYP93E1 in some cases). In addition, the polypeptide represented by SEQ ID NO:9 and the polypeptide represented by SEQ ID NO:11 are different from each other in terms of the 41st position and 61st position amino acids. The present inventors have revealed that the polynucleotide represented by SEQ ID NO:8 is coding for an enzyme protein which carries out hydroxylation of the 24-position of an oleanane type triterpene. Based on this knowledge, the inventors have conducted intensive efforts and accomplished the invention.

Accordingly, the invention relates to the following 1 to 17.

1. An expression vector having a polynucleotide which hybridizes with a complementary chain of the polynucleotide represented by SEQ ID NO:8 under a stringent condition and also encodes a polypeptide that has the activity of hydroxylating the 24-position of an oleanane type triterpene.

2. The expression vector described in the aforementioned 1, wherein the polynucleotide is the polynucleotide represented by SEQ ID NO:8.

3. A transformant in which a host is transformed with the expression vector described in the aforementioned 1 or 2.

4. The transformant described in the aforementioned 3, wherein the host is a microorganism.

5. The transformant described in the aforementioned 4, wherein the microorganism is a yeast.

6. An expression vector having a polynucleotide which hybridizes with a complementary chain of the polynucleotide represented by SEQ ID NO:8 under a stringent condition and also encodes a polypeptide that has the activity of hydroxylating the 24-position of an oleanane type triterpene, and having a β-amyrin synthase gene.

7. The expression vector described in the aforementioned 6, wherein the polynucleotide is the polynucleotide represented by SEQ ID NO:8.

8. A transformant in which a host is transformed with the expression vector described in the aforementioned 6 or 7.

9. The transformant described in the aforementioned 8, wherein the host is a microorganism.

10. The transformant described in the aforementioned 9, wherein the microorganism is a yeast.

11. A lanosterol synthase deficient yeast mutant strain deposited as FERM BP-10201.

12. A method for producing a polypeptide that has the activity of hydroxylating the 24-position of an oleanane type triterpene, which comprises a step of culturing the transformant described in any one of the aforementioned 3 to 5 and thereby producing the polypeptide described in the aforementioned 1.

13. A method for producing a polypeptide that has the activity of hydroxylating the 24-position of an oleanane type triterpene and a β-amyrin synthase, by culturing the transformant described in any one of the aforementioned 8 to 10, which comprises
1) a step for producing the polypeptide described in the aforementioned 1 and
2) a step for producing the β-amyrin synthase.

14. A method for producing an oleanane type triterpene in which the 24-position is hydroxylated, which comprises a step of allowing the transformant described in any one of the aforementioned 3 to 5 to act upon an oleanane type triterpene.

15. A method for producing an oleanane type triterpene in which the 24-position is hydroxylated, effected by culturing the transformant described in any one of the aforementioned 8 to 10.

16. A method for producing an oleanane type triterpene in which the 24-position is hydroxylated, effected by culturing the yeast mutant strain described in the aforementioned 11.

ADVANTAGE OF THE INVENTION

By the invention, it was able to reveal nucleotide sequence of the gene of an oleanane type triterpene 24-position hydroxylase and an amino acid sequence thereof. Also, the use of said gene by means of genetic engineering techniques renders possible large scale production of the enzyme protein as a gene product.

In addition, it became possible to effect hydroxylation of the 24-position of a triterpene, by the use of the produced enzyme protein or a transformant containing said enzyme protein. Also, it became possible to produce a triterpene in which the 24-position is hydroxylated, by the direct culturing using a transformant transformed with said gene and a β-amyrin synthase gene.

BEST MODE FOR CARRYING OUT THE INVENTION

As the oleanane type triterpene of the invention, β-amyrin, sophoradiol, soyasapogenols A and B and the like are known, but the oleanane type triterpene of the invention is not limited to the above case.

As the oleanane type triterpene in which the 24-position will be hydroxylated, β-amyrin and sophoradiol can be exemplified, but this is not limited to the above case, with the proviso that it is a compound in which the 24-position will be hydroxylated by the method of the invention. As the triterpene in which the 24-position is hydroxylated, soyasapogenols A and B can be exemplified, but not limited to soyasapogenols A and B, with the proviso that they are oxidation products by the invention.

According to the invention, an oleanane type triterpene in which the 24-position will be hydroxylated can be produced making use of the transcription and translation products of polynucleotide of the cytochrome P-450 gene CYP93E1, and equivalent forms thereof. In this connection, the equivalent forms mean those sequences which have the same function and hybridize under a stringent condition with a complementary chain of the sequence described in the cytochrome P-450 gene CYP93E1.

Regarding the "hybridize under a stringent condition", hybridization of a nucleotide can be verified by the use of a method (e.g., colony hybridization, plaque hybridization, Southern blot hybridization or the like) in which the hybridization is carried out using, as the probe, a part or entire portion (or a complementary chain thereof) of a DNA having the nucleotide sequence represented by cytochrome P-450 gene CYP93E1. Illustratively, a case in which hybridization is carried out at 55° C. in the presence of 0.5 mol/l of sodium chloride, and then 2×SSC solution (composition of 1×SSC solution consists of 150 mM NaCl, 15 mM sodium citrate, pH 7.0) is used can be exemplified.

The hybridization can be carried out in accordance with the method described in Molecular Cloning, A Laboratory Manual, edited by T. Maniatis et al, Cold Spring Harbor Laboratory, 1989, or the like. As a DNA which can be hybridized, a DNA that shows a homology of at least 80% or more, preferably 90% or more, more preferably 95% or more, with the nucleotide sequence represented by the cytochrome P-450 gene CYP93E1, when calculated using BLAST (National Center for Biotechnology Information), can be illustratively exemplified. In this connection, the homology according to the invention means the numerical value when parameters of BLAST are set to Wordsize: 3, Matrix: BLOSOM 62, Gap Costs: Existence: 11, Extension: 1.

In addition, the "polynucleotide which hybridizes with a complementary chain of the polynucleotide of the cytochrome P-450 gene CYP93E1 under a stringent condition and also encodes a polypeptide that has the activity of hydroxylating the 24-position of an oleanane type triterpene" illustratively includes a polynucleotide in which one or two or more nucleotides in the polynucleotide sequence of the cytochrome P-450 gene CYP93E1 are deleted, substituted, inserted or added, and which encodes a polypeptide that has the activity of hydroxylating the 24-position of an oleanane type triterpene. The number of nucleotides to be substituted in the polynucleotide sequence of the cytochrome P-450 gene CYP93E1 is not particularly limited, with the proviso that it is a number which satisfies the aforementioned homology and encodes a polypeptide that has the activity of hydroxylating the 24-position of an oleanane type triterpene.

Mutation on the polynucleotide of cytochrome P-450 gene CYP93E1 includes an artificial mutation in addition to mutations which are generated in the natural world. An example of the means for causing an artificial mutation is a method for obtaining a polynucleotide in which at least one of the deletion, substitution, insertion and addition is effected on one or two or more nucleotides, by means of a genetic engineering technique by introducing a random mutation or site-directed mutation using the polynucleotide of cytochrome P-450 gene CYP93E1. By using the mutant polynucleotide obtained in this manner, it becomes possible to obtain a polypeptide having different optimum temperature, heat stability, optimum pH, pH stability, substrate specificity and the like properties of the activity of this enzyme.

In addition, a polynucleotide which hybridizes with a complementary chain of the polynucleotide of the cytochrome P-450 gene CYP93E1 under a stringent condition and also encodes a polypeptide that has the activity of hydroxylating the 24-position of an oleanane type triterpene can also be obtained by a method in which a hybridization (e.g., colony hybridization, plaque hybridization, Southern blot hybridization or the like) is applied to other microorganisms, plants or animals capable of producing an oleanane type triterpene wherein the 24-position is hydroxylated (preferably a plant, more preferably a leguminous plant, most preferably a soybean, which can produce an oleanane type triterpene), using, as the probe, a part or entire portion (or a complementary chain thereof) of a nucleotide having the nucleotide sequence of the cytochrome P-450 gene CYP93E1, or by a method in which PCR is carried out using, as the probe, a part or entire portion (or a complementary chain thereof) of a nucleotide having the nucleotide sequence of the cytochrome P-450 gene CYP93E1, or the like.

In addition, the aforementioned polynucleotide can also be obtained by chemical synthesis based on the information of the nucleotide sequence. This method can be carried out by referring to the descriptions in Gene, vol. 60 (1), pp. 115-127 (1987).

In addition, the invention relates to a transformant prepared by transforming a host with a vector which can perform autonomous replication (preferably an expression vector) for harboring and/or expressing polynucleotide of the cytochrome P-450 gene CYP93E1 and equivalents thereof. Said vector may further contain a β-amyrin synthase gene in addition to the polynucleotide of cytochrome P-450 gene CYP93E1 and equivalents thereof.

As examples of the host, a microorganism, a plant, an animal and the like can be cited, though not particularly limited. As the microorganism, a yeast, *Escherichia coli* and the like can be exemplified, and a yeast is preferably used. As the animal, a silkworm can be exemplified. As the plant, a soybean can be exemplified. It is possible to provide a plant having increased content of an oleanane type triterpene in which the 24-position is hydroxylated, by transferring the vector of the invention into the plant.

As an example of the yeast to be transformed, there is a lanosterol synthase deficient yeast GIL 77 (Kushiro, T. et al., *Eur. J. Biochem.*, 256, 238-244, 1998). It becomes possible to culture-produce a triterpene in which the 24-position is hydroxylated, by integrating a cDNA corresponding to the aforementioned cytochrome P-450 gene CYP93E1 and a pea-derived β-amyrin synthase gene into a yeast expression vector pESC-ERA (mfd. by Stratagene), transforming the lanosterol synthase deficient yeast GIL 77 therewith, and effecting co-expression of the two genes.

As the expression vector, those which can perform autonomous replication in the host cell or can be integrated into chromosome, and have a promoter at a position where the polynucleotide of the invention can be transcribed, are used.

As the expression vector when the host cell is a microorganism, for example, pBluescript (mfd. by STRATAGENE), pUC18 (mfd. by Takara Bio), pUC118 (mfd. by Takara Bio), pUC19 (mfd. by Takara Bio), pUC119 (mfd. by Takara Bio) and the like can be exemplified.

Regarding the promoter, it may be any promoter which can effect the expression in *Escherichia coli*, a fungus and the like host cells. For example, a trp promoter ($P_{trp}$), a lac promoter ($P_{lac}$) and the like promoters derived from *Escherichia coli*, a phage and the like, and a Taka-amylase gene promoter, a TEF 1 gene promoter and the like promoters derived from an *Aspergillus* strain and the like can be cited.

In addition, an artificially designed and modified promoter and the like can also be used.

Regarding the method for transferring a recombinant vector, any method for transferring a polynucleotide into the aforementioned host cells can be used, and for example, a method which uses calcium ion [*Proc. Natl. Acad. Sci. USA*, 69, 2110 (1972)] and the like can be cited.

As the expression vector when a yeast strain is the host cell, for example, pAUR101 (mfd. by Takara Bio), pAUR112 (mfd. by Takara Bio), pI-RED1 (mfd. by TOYOBO) and the like can be exemplified.

As the promoter, it may be any promoter which can effect the expression in the yeast strain.

For example, a glycolytic pathway enzyme gene promoter, a Gal promoter and the like promoters can be cited.

Regarding the method for transferring a recombinant vector, any method for transferring a polynucleotide into a yeast strain can be used, and for example, the electroporation [*Methods. Enzymol.*, 194, 182 (1990)], the spheroplast method [*Proc. Natl. Acad. Sci. USA*, 84, 1929 (1978)], the lithium acetate method [*Journal of Bacteriology (J. Bacteriol.)*, 153, 163 (1983)] and the like can be cited.

Regarding the medium and culture conditions of host cells, it is possible to optionally select them in accordance with the conventionally known methods. When a microorganism is used as the host cell, the medium to be used for culturing the obtained transformant may be either a natural medium or a synthetic medium, with the proviso that it is a medium which contains a carbon source, a nitrogen source, inorganic salts and the like that can be assimilated by said microorganism and can carry out culturing of the transformant efficiently.

As the carbon source, potato dextrose, glucose, sucrose, soluble starch, glycerol, dextrin, molasses, organic acids and the like can be used. As the nitrogen source, ammonium sulfate, ammonium carbonate, ammonium phosphate, ammonium acetate and the like inorganic salts or ammonium salts of organic acids, other nitrogen compounds, peptone, yeast extract, corn steep liquor, casein hydrolysates and meat extract can be used. As the inorganic salts, potassium primary phosphate, potassium secondary phosphate, magnesium phosphate, magnesium sulfate, sodium chloride, ferrous sulfate, manganese sulfate, copper sulfate, calcium carbonate and the like can be used.

When the host cell is a silkworm, the polypeptide of the invention can be expressed, for example, by a conventionally known method which uses a baculovirus expression system [*Appl. Microbiol. Biotechnol.*, 62, 1-20 (2003)]. Also, when a plant transformed with the polypeptide of the invention using a plant cell as the host is obtained, for example, a direct gene transfer which uses a Ti plasmid or a binary plasmid system of *Agrobacterium tumefaciens*, an Ri plasmid of *Agrobacterium rhizogenes* or polyethylene glycol or the electroporation is effective [*Methods in Molecular Biology*, 267, *Recombinant Gene Expression*, 329-50 (2004)].

In addition, when a transformant transferred with an expression vector having an inducible promoter is cultured, an inducer may be added to the medium as occasion demands. For example, isopropyl-β-D-thiogalactopyranoside or the like can be added to the medium when the lac promoter is used, or indoleacrylic acid or the like when the trp promoter is used.

In this connection, regarding the method for expressing the polypeptide of the invention other than its direct expression, it can be carried out in accordance with the method described in Molecular Cloning Second Edition or the like.

An oleanane type triterpene in which the 24-position is hydroxylated can be produced using the transformant described in the aforementioned 3 to 5. The transformant is cultured in the medium adding the oleanane type triterpene as a substrate. Thus obtained 24-position-hydroxylated compound is extracted with ethyl acetate, ether or the like organic solvent and purified using silica gel or ODS.

In addition, an oleanane type triterpene in which the 24-position is hydroxylated can also be produced by preparing a cell-free extract from the culture medium of the transformant. In that case, the collected cells are suspended in a suspending liquid, the resulting cells are disrupted using a homogenizer, a sonic disintegrator or a French press or the like and then centrifuged to obtain a cell-free extract. In order to prevent inactivation of the polypeptide, an antioxidant, an enzyme stabilizer, a polyphenol adsorbing agent, a metal ligand and the like can be added to the buffer liquid. It is effective to purify the polypeptide for further increase the specific activity, and centrifugation by a centrifuge, salting out with ammonium sulfate or the like, gel filtration, ion exchange chromatography, affinity chromatography, electrophoresis and the like techniques can be used alone or in combination.

The oleanane type triterpene to be used as the substrate and a coenzyme are added to the thus obtained polypeptide-containing buffer and incubated at from 15 to 40° C., preferably at from 20 to 37° C. As the coenzyme, NADH or NADPH can be used, and an NADPH reconstruction system which uses glucose 6-phosphate and glucose-6-phosphate dehydrogenase can be used also to carry out the hydroxylation reaction by adding an NADPH-P-450 reductase other than the NADPH-P-450 reductase produced by the transformant cells.

When the transformants described in the aforementioned 8 to 10 are used, an oleanane type triterpene is produced making use of the 2,3-oxidosqualene produced by the transformant cells themselves, so that the 24-position-hydroxylated oleanane type triterpene can be produced without adding the oleanane type triterpene from the outside moiety. The thus obtained 24-position-hydroxylated compound is extracted with ethyl acetate, ether or the like organic solvent and then purified using silica gel or ODS.

Outlines of the examples of the invention are described in the following.

Seven species of soybean-derived EST and cytochrome P-450 clones whose functions are unidentified but complete length nucleotide sequences have been reported (GenBank Accession Numbers: AF 135485, Y 10491, Y 10982, Y 10983, Y 10493 and AF 022459, and TIGR Accession Number: TC 100921) were selected. Among them, CYP93E1 (GenBank Accession Numbers AF 135485) showed the activity, and the polynucleotide of SEQ ID NO:8 which showed high homology therewith is described in the following. A cDNA which corresponds to the CYP93E1 (SEQ ID NO:8) was amplified by the RT-PCR method from mRNA prepared from soybean sprouts and integrated into a yeast expression vector pESC-ERA (mfd. by Stratagene), and a lanosterol synthase deficient yeast GIL 77 (Kushiro, T. et al., *Eur. J. Biochem.*, 256, 238-244, 1998) was transformed therewith to carry out function analysis. Cell-free extracts of the yeast transformants were allowed to react with β-amyrin, and the products were acetylated and analyzed by GCMS. As a result, 3,24-diacetoxy-12-oleanene was detected.

In the same manner, cell-free extracts of the yeast transformants were allowed to react with sophoradiol, and the products were acetylated and analyzed by GCMS. As a result, triacetylsoyasapogenol B was detected.

β-Amyrin was added to the culture medium of yeast transformants and allowed to undergo the reaction, and then the cells were collected. Fat-soluble fractions were extracted and acetylated and then analyzed by GCMS. As a result, 3,24-diacetoxy-12-oleanene was detected.

The aforementioned cDNA of SEQ ID NO:8 and pea-derived β-amyrin synthase gene were integrated into a yeast expression vector pESC-ERA (mfd. by Stratagene), and the lanosterol synthase deficient yeast GIL 77 was transformed therewith, thereby effecting co-expression of the two genes. This transformed yeast, named GIL77/pESC•PSY•CYP93E1, has been deposited on Feb. 6, 2004, as FERM P-19675 (transferred to FERM BP-10201 on Jan. 6, 2005) in international Patent Organism Depositary, National Institute of Advanced Industrial Science and Technology (postal code 305-8566; Central 6, 1-1-1 Higashi, Tsukuba, Ibaraki, Japan).

The transformed yeast was cultured, and the cells were collected. Fat-soluble fraction was extracted and acetylated and then analyzed by GCMS. As a result, 3,24-diacetoxy-12-oleanene was detected.

In the same manner, the aforementioned cDNA of SEQ ID NO:8 and an *Arabidopsis thaliana*-derived mixed triterpene synthase gene were integrated into the yeast expression vector pESC-ERA (mfd. by Stratagene), and the lanosterol synthase deficient yeast GIL 77 was transformed therewith, thereby effecting co-expression of the two genes.

The transformed yeast was cultured, and the cells were collected. Fat-soluble fraction was extracted and acetylated and then analyzed by GCMS. As a result, 3,24-diacetoxy-12-oleanene was detected. Other diacetoxytriterpenes were not detectable.

Based on the above results, the hydroxylation activity on the 24-position of sophoradiol and β-amyrin, which is not detected originally, was confirmed, so that it was able to reveal that the SEQ ID NO:8 is a gene coding for an enzyme which hydroxylates the 24-position of an oleanane type triterpene. On the other hand, this activity was not detected in the other 6 P-450 genes examined in the same manner.

The following describes the invention further in detail based on examples, but the invention is not limited to these examples.

EXAMPLE 1

(1) Preparation of Soybean Sprout cDNA

Total RNA was extracted by the phenol/chloroform method from soybean (early ripening green soybean, Atariya Noen) young leaves after 14 days of soaking in water. By using this as the template, cDNA was prepared using a reverse transcriptase Superscript II (mfd. by GIBCO BRL) and the primer shown in SEQ ID NO:1.

(2) Amplification of Polynucleotide of SEQ ID NO:8

Using the cDNA prepared in the aforementioned (1) as the template, and the oligo DNA fragments which correspond to the N-terminus and C-terminus of the polypeptide, shown in SEQ ID NOs:2 and 3, as the primers, PCR (30 cycles, Ex Taq DNA polymerase manufactured by Takara Shuzo) was carried out at an annealing temperature of 65° C. to obtain a complete length clone of CYP93E1 (SEQ ID NO:8).

(3) Construction of pESC-CYP93E1 and Preparation of Transformed Yeast

The complete length clone obtained in the above (2) was treated with SpeI and ClaI and integrated into the SpeI-ClaI site of a yeast expression vector pESC-URA (mfd. by Stratagene) This was named pESC-CYP93E. pESC-CYP93E was transferred into a yeast strain INVSC 2 (mfd. by Invitrogen) using Frozen-EZ Yeast Transformation II (mfd. by Zymo Research).

(4) In Vitro Enzyme Activity Test

The transformed yeast was inoculated into 20 ml of SC-U medium (Methods in yeast Genetics, A Laboratory Course Manual, Cold Spring Harbor Laboratory Press, 1990) containing 2% raffinose instead of glucose and cultured at 30° C. and at 220 rpm for 18 hours. Hemin (13 μg/ml in final concentration) and galactose (2% in final concentration) were added thereto to carry out the culturing for 20 hours under the same conditions. The cells were collected by centrifugation, transferred into a 2 ml capacity screw vial and again suspended by adding 100 μl of an extraction buffer (prepared by adding 10% sucrose, 1 mM EDTA and 14 mM 2-mercaptoethanol to 50 mM potassium phosphate buffer of pH 7.5). Glass beads having a diameter of from 0.4 to 0.6 mm (mfd. by Iuchi Seieido) were washed with dilute hydrochloric acid and added thereto. By cooling to 4° C., disruption of the cells were carried out using MINI-BEADBREADER (mfd. by BIOSPEC). This was further mixed with 400 μl of the extraction buffer and thoroughly stirred, and then centrifuged at 3500 g for 5 minutes while cooling to 4° C. to recover about 400 μl of the supernatant as a crude enzyme liquid. To this were added 100 μl of a concentrated reaction buffer (prepared by adding 10 mM of NADPH, 75 mM of glucose-6-phosphate (G6P) and 2.5 U/ml of glucose-6-phosphate dehydrogenase (G6PDH) to the extraction buffer) and 5 μl of 10 mM β-amyrin methanol solution. This was allowed to undergo the reaction at 30° C. for 6 hours. After adding 10 μl of 12 N hydrochloric acid, this was concentrated by carrying out extraction of the fat-soluble components twice using 500 μl of ethyl acetate. Acetylation of the extract was carried out by adding 20 μl of pyridine and acetic anhydride thereto and allowing this to stand overnight. The reaction was stopped by adding 200 μl of 50% methanol aqueous solution thereto, and this was concentrated by carrying out extraction twice using 200 μl of hexane (1)). As a control test, samples were prepared by the same method on 2) a cases in which a crude enzyme liquid derived from a transformant prepared using pESC-URA was used, 3) a cases in which β-amyrin as the substrate was not added, 4) a cases in which the reaction was carried out using a crude enzyme liquid heat-treated at 100° C. for 5 minutes, and 5) a cases in which the same amount of glucose was added instead of galactose for the purpose of inhibiting the GAL 1 promoter of pESC-CYP93E1. Each of them was dissolved in 20 μl of hexane and 1 μl portion thereof was subjected to GC-MS analysis (a gas chromatographic mass spectrometer GCMS-QP 2010 mfd. by Shimadzu Corp., column: Rtx-5MS mfd. by RESTEK, inner diameter 0.25 mm membrane thickness 0.25 μm length 30 m, temperature rising program: 3 minutes of holding at 230° C., temperature rising at 10° C./minute, 8 minutes of holding at 330° C.). Total ion monitoring (TIM) was carried out, and the presence or absence of the product was analyzed by a mass chromatogram of m/z=218 (base peak of 3β,24-diacetoxy-12-oleanene). Formation of 3β,24-diacetoxy-12-oleanene was not found by the TIM (results are not described). However, 3β,24-diacetoxy-12-oleanene was observed in the mass chromatogram of m/z=218 by the condition of 1) (FIG. 1). Based on this result, it was confirmed that the CYP93E1 translation product has the activity to perform hydroxylation of the 24-position of β-amyrin.

Next, in order to examine its reactivity for sophoradiol, the enzyme reaction was carried out in the same manner using sophoradiol (5 μl, 10 mM) as the substrate, and GCMS analysis was carried out in the same manner as in the above. The peak of triacetyl soyasapogenol B was found by the mass chromatogram analysis (m/z=216 base peak of triacetyl soyasapogenol B) of the product under the reaction condition of the aforementioned 1) (FIG. 2). Based on this result, it was revealed that the CYP93E1 translation product has the activity to perform hydroxylation of the 24-position of not only β-amyrin but also sophoradiol.

(5) In Vivo Enzyme Activity Test

The transformed yeast was inoculated into 20 ml of the SC-U medium containing 2% raffinose instead of glucose and cultured at 30° C. and at 220 rpm for 18 hours. Hemin (13 μg/ml in final concentration) and galactose (2% in final concentration) were added thereto, and 10 μl of 10 mM β-amyrin methanol solution was further added thereto as the substrate. In order to supply oxygen, the upper part of the Falcon tube was sealed with a cotton plug, and this was further cultured for 24 hours aseptically and aerobically. The cells were collected by centrifugation and transferred into a 2 ml capacity screw vial. A 250 μl portion of 40% potassium hydroxide aqueous solution and 250 μl of methanol were added thereto, and the mixture was thoroughly stirred and heat-treated at 100° C. for 5 minutes. This was concentrated by carrying out extraction of the fat-soluble components twice using 500 μl of hexane. Acetylation of the extract was carried out by adding 20 μl of pyridine and acetic anhydride thereto and allowing this to stand overnight. The reaction was stopped by adding 200 μl of 50% methanol aqueous solution thereto, and this was concentrated by carrying out extraction twice using 200 μl of hexane (1)). As a control test, samples were prepared by the same method on 2) a cases in which a transformant prepared using pESC-URA was used, 3) a cases in which β-amyrin as the substrate was not added, and 4) a cases in which the same amount of glucose was added instead of galactose for the purpose of inhibiting the GAL 1 promoter of pESC-CYP93E1. Each of them was dissolved in 10 μl of hexane, and a 1 μl portion thereof was subjected to GC-MS analysis under the same condition as in the (4) (the conditions are the same as the test of (4)). The peak of 3β,24-diacetoxy-12-oleanene was observed by the TIM under the condition of 1) (FIG. 3), and the MS cleavage pattern of the peak coincided with the standard preparation (FIG. 4). Based on the results of determination by peak area ratio of TIM, it can be considered that several μg of 3β, 24-dihydroxy-12-oleanene is obtained when cultured using 1 liter of the medium under the same conditions of the above case (addition of about 2 mg of β-amyrin).

(6) Construction of Expression Plasmid pESC-PSY

Using a plasmid integrated with a pea-derived β-amyrin synthase gene PSY (AB034802, *Eur. J. Biochem.*, 267, 3543-3460, 2000) as the template, and using the oligo DNA fragments shown in SEQ ID NOs:4 and 5 which correspond to the N-terminus and C-terminus of the polypeptide as the primers, PCR (30 cycles, Ex Taq DNA polymerase manufactured by Takara Shuzo) was carried out at an annealing temperature of 58° C. to obtain a PSY fragment in which SalI and NheI sites were respectively introduced into the N-terminus and C-terminus. The pESC-PSY was prepared by introducing this into SalI and NheI sites of pESC-URA, and the β-amyrin synthase activity was confirmed by a conventionally known method (*Eur. J. Biochem.*, 267, 3543-3460, 2000).

(7) Construction of Expression Plasmid pESC-PSY-CYP93E1 and Preparation of Transformed Yeast pESC-PSY and pESC-CYP93E1 were digested with SalI and ClaI. By ligating the thus obtained fragment containing PSY and the fragment containing CYP93E1, a PSY- and CYP93E1-co-expressing plasmid pESC-PSY-CYP93E1 was constructed. A transformant was obtained by transferring this into a yeast strain GIL 77 using Frozen-EZ Yeast Transformation II.

(8) Co-Expression Test of PSY and CYP93E1

The transformed yeast strain was inoculated into a medium prepared by supplementing 20 ml of the SC-U medium containing 2% glucose as the carbon source with hemin (13 μg/ml in final concentration), ergosterol (20 μg/ml in final concentration) and Tween 80 (5 mg/ml in final concentration), and cultured at 30° C. and 220 rpm for 1.5 days. The medium was exchanged with a medium prepared by adding hemin (13 μg/ml in final concentration), ergosterol (20 μg/ml in final concentration) and Tween 80 (5 mg/ml in final concentration) to 20 ml of the SC-U medium containing 2% galactose as the carbon source, and then the culturing was further continued at 30° C. and 220 rpm for 1 day. The cells were transferred into a 50 mM potassium phosphate buffer of pH 7.5, mixed with hemin (13 μg/ml in final concentration) and glucose (3% in final concentration) and further incubated at 30° C. and at 220 rpm for 1 day. An acetylated sample for GC-MS analysis was prepared in the same manner as the test method in (4). As a control test, samples were prepared by the same method on a transformant prepared using pESC-URA and a transformant prepared using pESC-PSY and pESC-CYP93E1. Each of these samples was dissolved in 1000 μl of hexane, and a 1 μl portion of this was subjected to GC-MS analysis (conditions are the same as in the test in (4)). As shown in FIG. 5, a peak corresponding to 3β,24-diacetoxy-12-oleanene was observed by TIM only when the yeast strain transformed with pESC-PSY-CYP93E1 was used. As a result of the determinative analysis by peak area ratio, it can be considered that several hundred μg of 3β,24-dihydroxy-12-oleanene is obtained when cultured using 1 liter of the medium under this condition.

(9) Large Scale (1 L) Culturing of GIL77/pESC-PSY-CYP93E1

The transformed yeast strain was inoculated into a 500 ml capacity conical flask charged with 250 ml of a medium prepared by adding hemin (13 μg/ml in final concentration), ergosterol (20 μg/ml in final concentration) and Tween 80 (5 mg/ml in final concentration) to 250 ml of the SC-U medium containing 2% raffinose as the carbon source. This was prepared for 4 flasks, and 1 liter in total volume of the culturing was carried out. After culturing at 30° C. and at 220 rpm for 20 hours, this was supplemented with galactose (2% in final concentration) and further cultured at 30° C. and at 220 rpm for 20 hours. The entire cells were transferred into 100 ml of a 50 mM potassium phosphate buffer of pH 7.5, mixed with hemin (13 μg/ml in final concentration) and glucose (3% in final concentration) and further incubated at 30° C. and at 220 rpm for 1 day.

(10) Isolation of Product from 1 Liter Culture of GIL 77/pESC-PSY-CYP93E1

The cells were collected from the culture mixture obtained in (9), mixed with 50 ml of 40% potassium hydroxide aqueous solution and 50 ml of methanol and heated under reflux for 1 hour. Extraction of the fat-soluble fraction was carried out using 50 ml of hexane. The hexane fraction was thoroughly washed 3 times with 50 ml of saturated sodium bicarbonate aqueous solution. The extraction was carried out by repeating this operation 3 times to obtain about 23 mg of the fat-soluble fraction.

This was purified by two steps of silica gel flash column chromatography. Firstly, the aforementioned fat-soluble fraction was dissolved in benzene and purified using a silica gel FC-40 (4 g, mfd. by Wako Pure Chemical Industries) and a hexane-ethyl acetate solvent system. Subsequently, said fraction was purified using the silica gel FC-40 (2 g) and a benzene-ethyl acetate solvent system to obtain 0.55 mg of 3β,24-dihydroxy-12-oleanene.

(11) Construction of expression plasmid pESC-YUP43

A plasmid integrated with an *Arabidopsis thaliana*-derived multifunctional triterpene synthase gene YUP43 (*Tetrahedron Lett.*, 41, 7705-7710, 2000) which provides 9 species of triterpene including β-amyrin was used as the template, and using the oligo DNA fragments shown in SEQ ID NOs:6 and 7 which correspond to the N-terminus and C-terminus of the polypeptide as the primers, PCR (annealing temperature 58° C., 30 cycles, Ex Taq DNA polymerase manufactured by Takara Shuzo) was carried out to obtain a YUP43 fragment in which SalI and NheI sites were respectively introduced into the N-terminus and C-terminus. The pESC-YUP43 was prepared by introducing this into SalI and NheI sites of pESC-URA, and the multifunctional triterpene synthase activity was confirmed by a conventionally known method (*Tetrahedron Lett.*, 41, 7705-7710, 2000).

(12) Construction of Expression Plasmid pESC-YUP43-CYP93E1 and Preparation of Transformed Yeast Plasmids pESC-YUP43 and pESC-CYP93E1 were digested with SalI and ClaI. By ligating the fragment containing YUP43 and the fragment containing CYP93E1, a YUP43- and CYP93E1-co-expressing plasmid pESC-YUP43-CYP93E1 was constructed. A transformant was obtained by transferring this into a yeast strain GIL 77 using Frozen-EZ Yeast Transformation II.

(13) Co-Expression Test of Polypeptides of Transcription and Translation Products of YUP43 and Polynucleotide of SEQ ID NO:8

By the same method of (8), samples were prepared from transformants respectively obtained using pESC-URA, pESC-YUP43, pESC-CYP93E1 and pESC-YUP43-CYP93E1. Each of them was dissolved in 1000 μl of hexane, and a 1 μl portion thereof was subjected to GC-MS analysis (conditions are the same as in the test of (4)). As shown in FIG. 7, a peak of 3β,24-diacetoxy-12-oleanene was observed by TIM only when the yeast strain transformed with pESC-YUP43-CYP93E1 was used. Since the produced amount of β-amyrin by YUP43 was lower than that by PSY, produced amount of 3β,24-diacetoxy-12-oleanene was decreased in comparison with the pESC-PSY-CYP93E1 transformant. On the other hand, peaks considered to be hydroxylation forms of other triterpenes (lupeol, butyrospermol, tirucalladienol, taraxasterol, pseudotaraxasterol, baureelenol, α-amyrin and multiflorenol) were equal to or lower than the detection limit.

While the invention has been describe in detail and with reference to specific embodiments thereof, it will be apparent to one skilled in the art that various changes and modifications can be made therein without departing from the spirit and scope of the invention.

This application is based on a Japanese patent application filed on Feb. 25, 2004 (Japanese Patent Application No. 2004-049123), the entire contents thereof being thereby incorporated by reference.

INDUSTRIAL APPLICABILITY

By the invention, it became possible to handle, by a genetic engineering technique, an enzyme which carries out hydroxylation of the 24-position of an oleanane type triterpene. Accordingly, the use of a cell into which said hydroxylase gene was integrated renders possible its use in, for example, the production of the hydroxylase by a yeast strain, application of hydroxylation reaction, microbial production of a plant triterpene and the like. In addition, by integrating the hydroxylase gene into a plant, there becomes a possibility of applying it into the agricultural field, such as increase of the production of soyasapogenol or the like triterpene.

SEQUENCE LISTING

Figure 1:
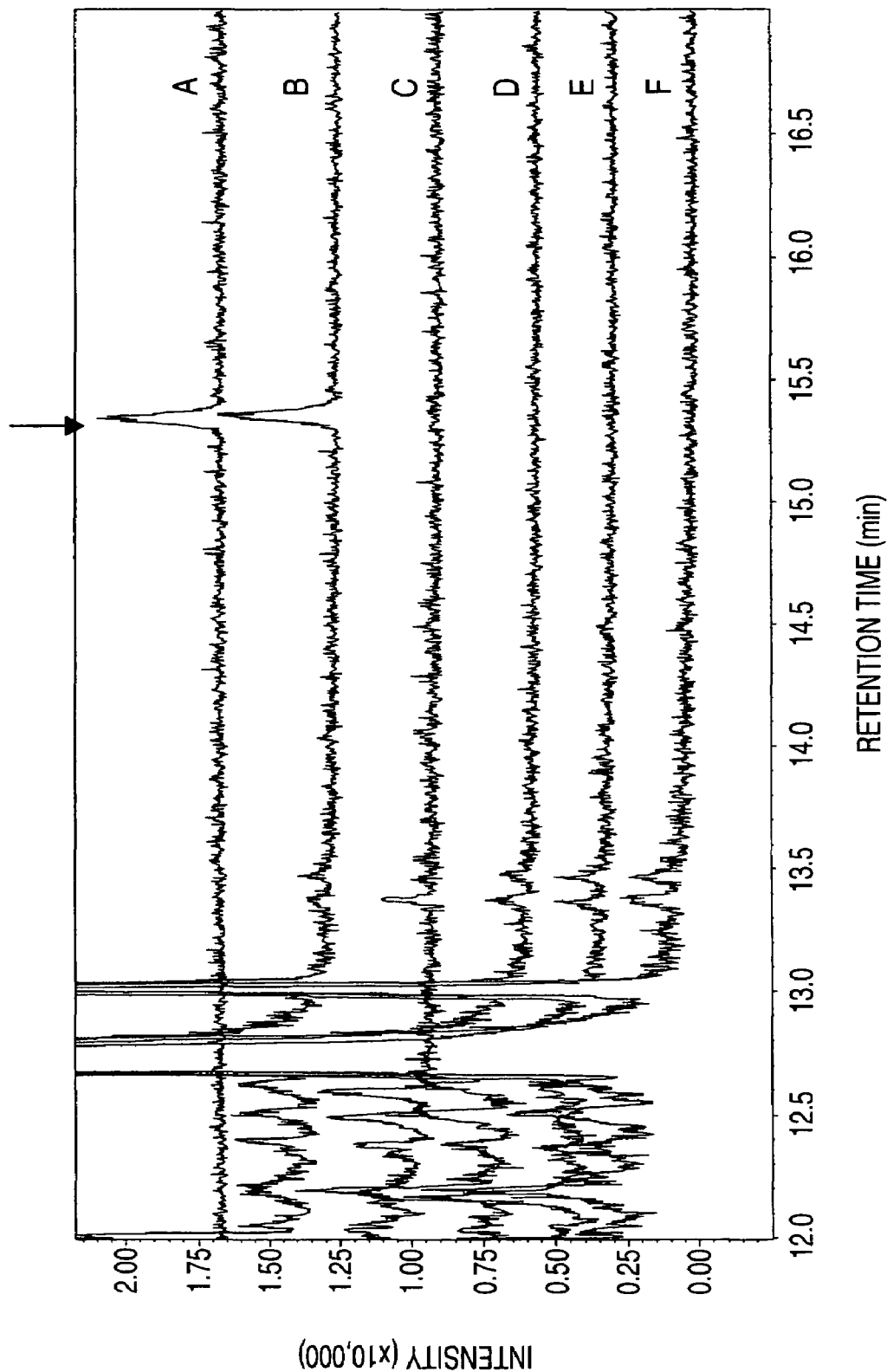
[FIG. 1] shows β-amyrin 24-position hydroxylation activity (in vitro) by the translation product of SEQ ID NO:8. More illustratively, it shows a mass chromatogram monitoring m/Z=218 which was analyzed by GC-MS after acetylation of the product. A to F show the following results. A: standard sample of 3β,24-diacetoxy-12-oleanene. B: a product obtained by allowing a crude enzyme liquid prepared from a yeast strain transformed with pESC-CYP93E1 to react with β-amyrin in the coexistence of an NADPH regeneration system. C: a product of the reaction of B carried out by removing β-amyrin from the reaction system. D: a product of the reaction of B carried out by using heat-denatured crude enzyme liquid. E: the yeast strain transformed with pESC-CYP93E1 was cultured by adding glucose, other conditions are the same as in B. F: a crude enzyme liquid prepared from a yeast strain transformed with a void plasmid pESC-URA was used, other conditions are the same as in B.
Figure 2:
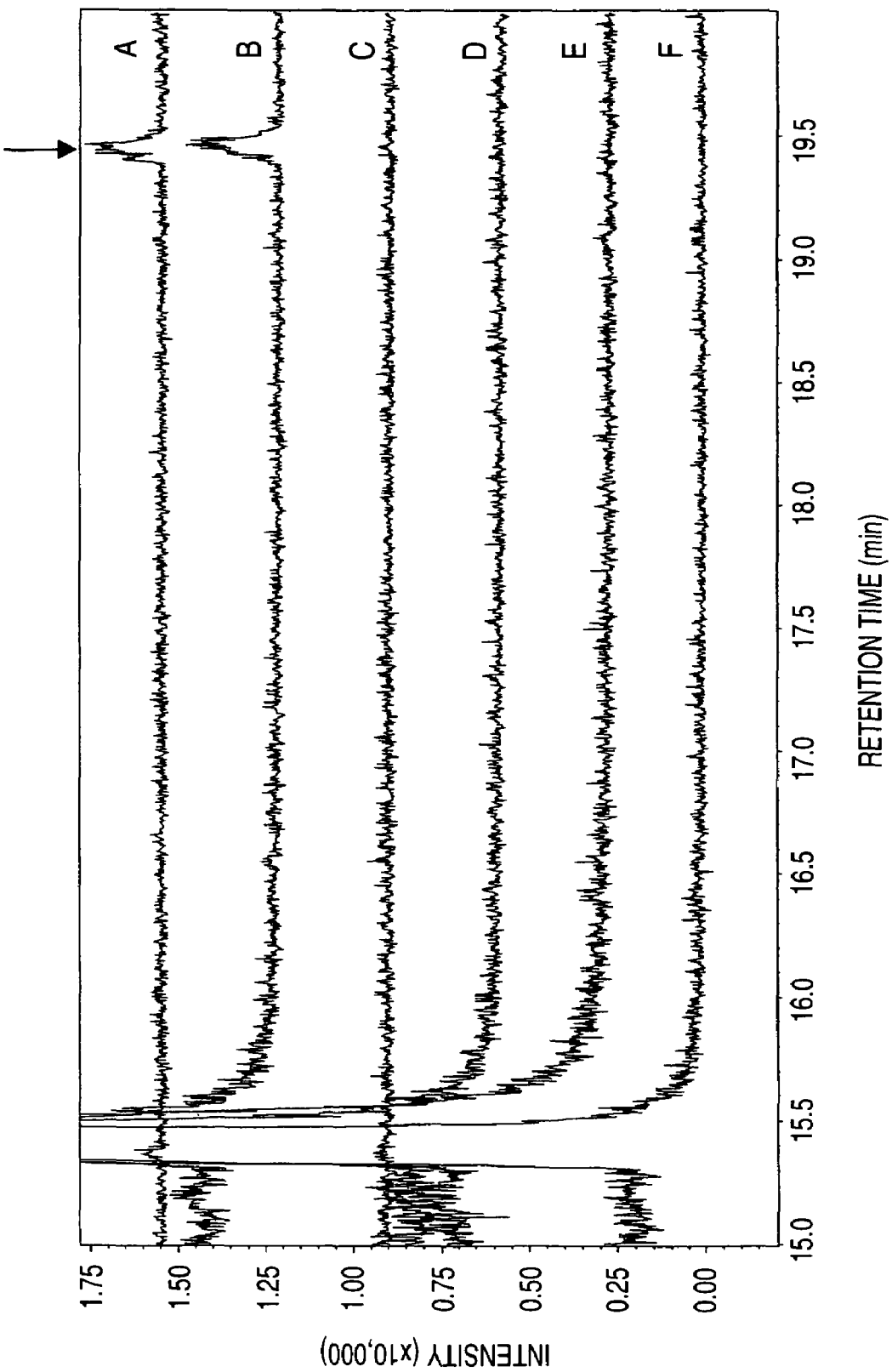
[FIG. 2] shows sophoradiol 24-position hydroxylation activity (in vitro) by the translation product of SEQ ID NO:8. More illustratively, it shows a mass chromatogram monitoring m/Z=216 which was analyzed by GC-MS after acetylation of the product. A to F show the following results. A: standard sample of triacetyl soyasapogenol B. B: a product obtained by allowing a crude enzyme liquid prepared from a yeast strain transformed with pESC-CYP93E1 to react with sophoradiol in the coexistence of an NADPH regeneration system. C: a product of the reaction of B carried out by removing sophoradiol from the reaction system. D: a product of the reaction of B carried out by using heat-denatured crude enzyme liquid. E: the yeast strain transformed with pESC-CYP93E1 was cultured by adding glucose, other conditions are the same as in B. F: a crude enzyme liquid prepared from a yeast strain transformed with a void plasmid pESC-URA was used, other conditions are the same as in B.
Figure 3:
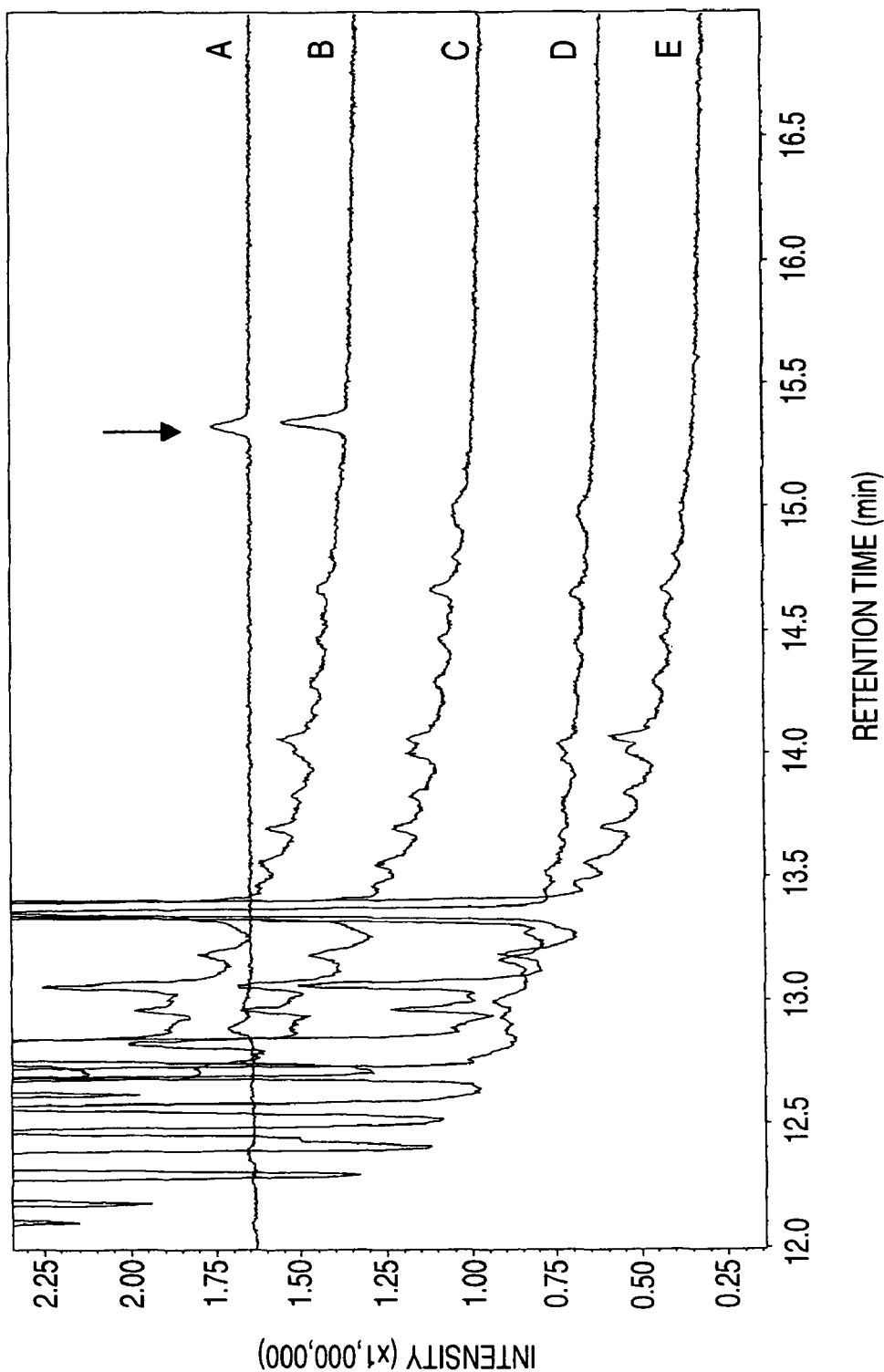
[FIG. 3] shows 24-position hydroxylation activity (in vivo) product of β-amyrin by the translation product of SEQ ID NO:8. More illustratively, it shows a chromatogram by TIM through GC-MS after acetylation of the product. A to E show the following results. A: standard sample of 3β,24-diacetoxy-12-oleanene (20 pmol) B: a product obtained by adding β-amyrin to a yeast strain transformed with pESC-CYP93E1. C: a case in which β-amyrin was not added, other conditions are the same as in B. D: the transformed yeast was cultured by adding glucose, other conditions are the same as in B. E: β-amyrin was added to a yeast strain transformed with a void plasmid pESC-URA, other conditions are the same as in B.
Figure 4:
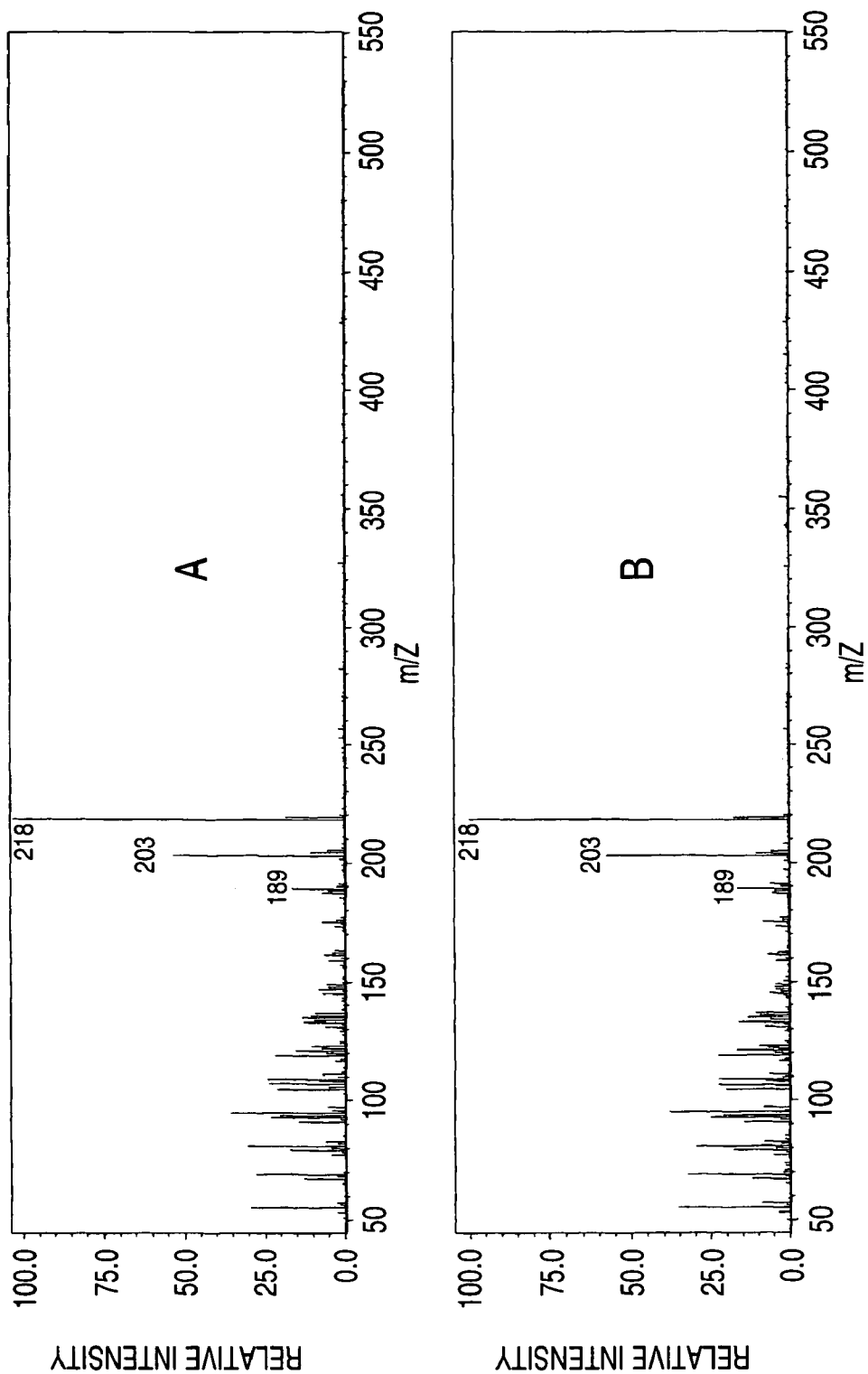
[FIG. 4] shows β-amyrin 24-position hydroxylation activity (in vivo) by the translation product of SEQ ID NO:8. A and B show the following results. A: a mass spectrum of the peak at a retention time of 15.35 minutes, detected in B of FIG. 3. B: a mass spectrum of A of FIG. 3 (standard sample of 3β,24-diacetoxy-12-oleanene).
Figure 5:
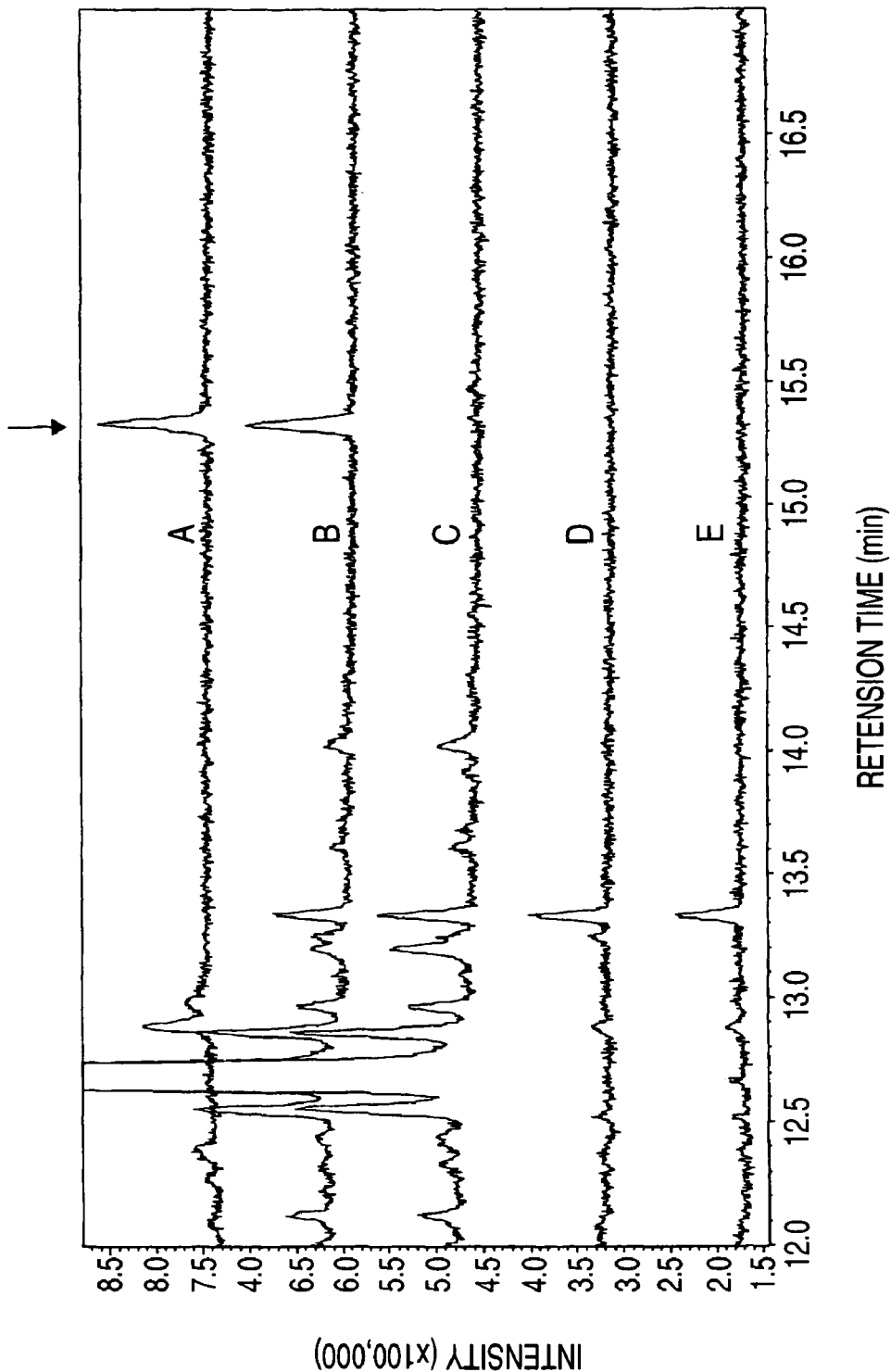
[FIG. 5] shows production of 3β,24-dihydroxy-12-oleanene by co-expression of CYP93E1 and β-amyrin synthase (PSY) More illustratively, it shows a chromatogram by TIM through GC-MS analysis after acetylation of the fat-soluble fraction obtained from respective transformed yeast (GIL 77). A to E show the following results. A: standard sample of 3β,24-diacetoxy-12-oleanene (20 pmol) B: an extract of yeast strain transformed with pESC-PSY-CYP93E1. C: an extract of yeast strain transformed with pESC-PSY. D: an extract of yeast strain transformed with pESC-CYP93E1. E: an extract of yeast strain transformed with pESC-URA.
Figure 6:
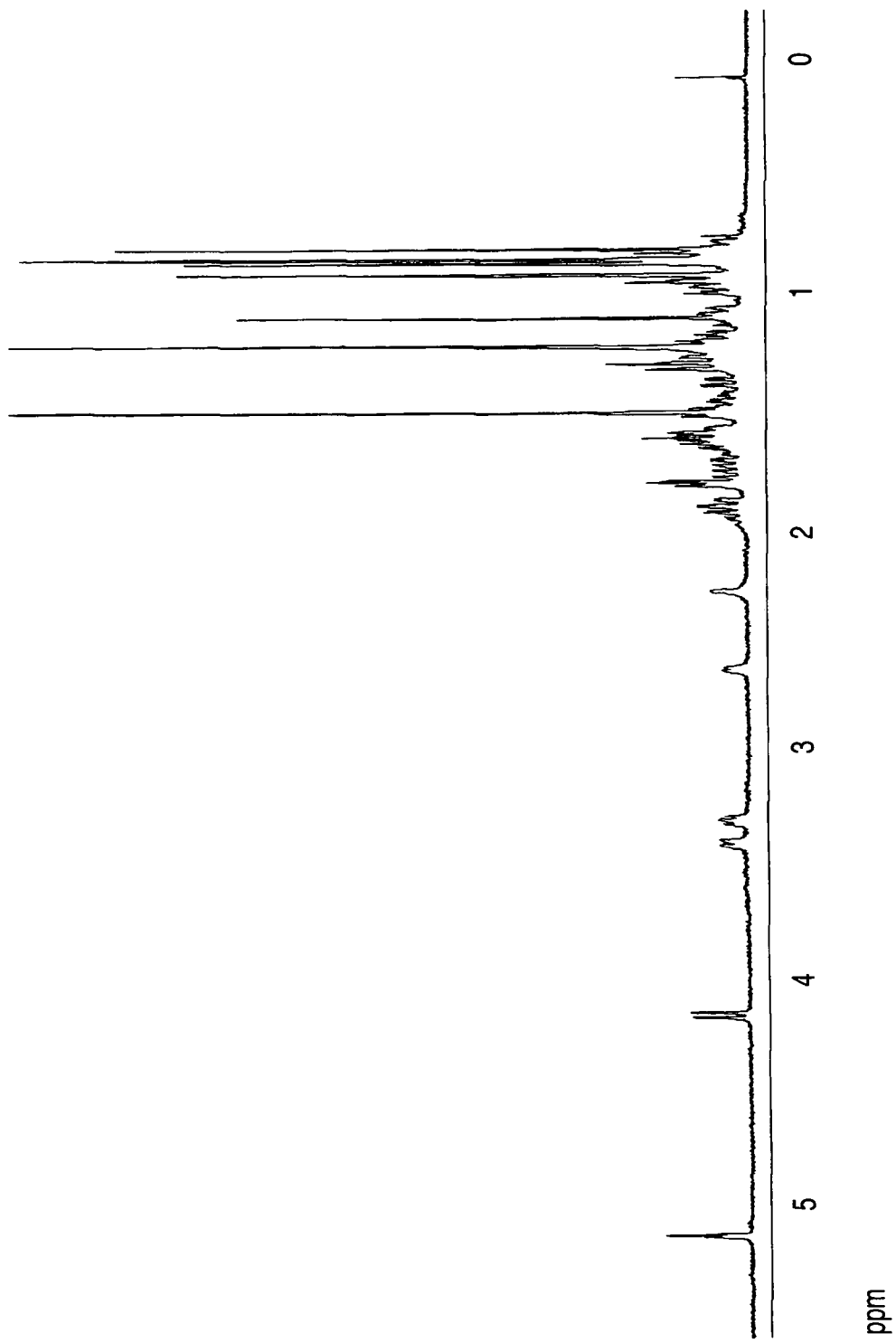
[FIG. 6] shows $^1$H-NMR of the product obtained from 1 liter of culture medium of GIL 77/pESC-PSY-CYP93E1.
Figure 7:
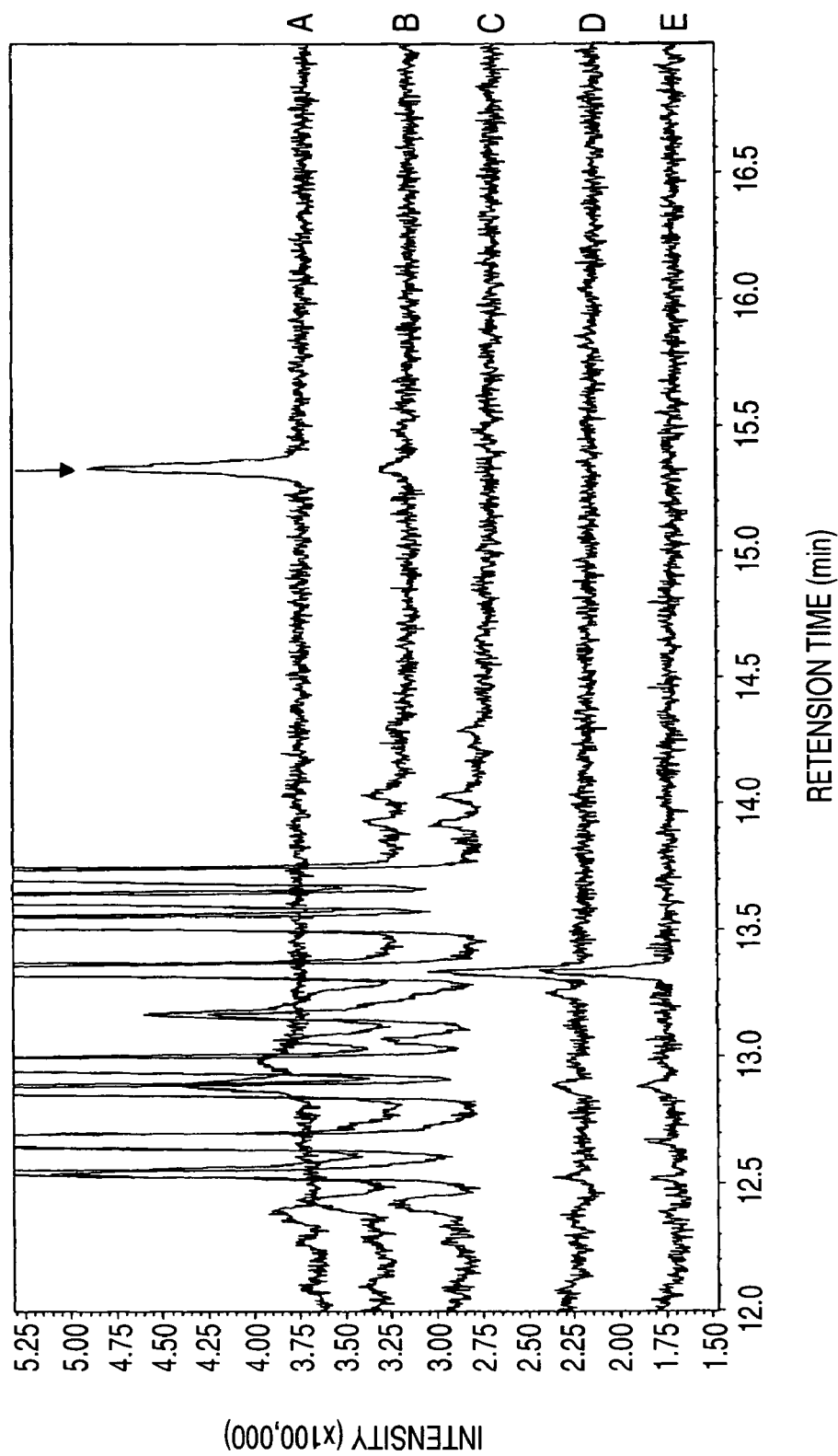
[FIG. 7] shows production of 3β,24-dihydroxy-12-oleanene by co-expression of the translation product of SEQ ID NO:8 and a multifunctional triterpene synthase (YUP43) More illustratively, it shows a chromatogram by TIM through GC-MS analysis after acetylation of the fat-soluble fraction obtained from respective transformed yeast (GIL 77). A to E show the following results. A: standard sample of 3β,24-diacetoxy-12-oleanene (20 pmol) B: an extract of yeast strain transformed with pESC-YUP43-CYP93E1. C: an extract of yeast strain transformed with pESC-YUP43. D: an extract of yeast strain transformed with pESC-CYP93E1. E: an extract of yeast strain transformed with pESC-Ura.

```
<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gactcgagtc gacaacgatt tttttttttt tt                                     32

<210> SEQ ID NO 2
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
aaacactagt atgctagaca tcaaaggcta c                                   31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttcaatcgat tcaggcagcg aacggagtga a                                   31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttcgtcgac aagatgtgga ggttgaagat a                                   31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtccgctagc tcaaggcaaa ggaactcttc t                                   31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagggtcgac attatgtgga agttgaagat a                                   31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taaggctagc ctaaagatct tgatgagttg c                                   31

<210> SEQ ID NO 8
<211> LENGTH: 1542
<212> TYPE: DNA
<213> ORGANISM: Soybean
<220> FEATURE:
```

-continued

```
<221> NAME/KEY: CDS
<222> LOCATION: (1)..(1542)

<400> SEQUENCE: 8 atg cta gac atc aaa ggc tac ctc gta ctc ttc ttc cta tgg ttc ata       48
Met Leu Asp Ile Lys Gly Tyr Leu Val Leu Phe Phe Leu Trp Phe Ile
1               5                   10                  15 tca acc att ctg ata cgt tcc atc ttc aag aaa cca cag cgt cta aga       96
Ser Thr Ile Leu Ile Arg Ser Ile Phe Lys Lys Pro Gln Arg Leu Arg
            20                  25                  30 ctc cca ccg ggt cct cca att tca gta ccc ttg ctg gga cac gcg cca      144
Leu Pro Pro Gly Pro Pro Ile Ser Val Pro Leu Leu Gly His Ala Pro
        35                  40                  45 tat ctc cgt tca ctg ctc cac caa gcc ttg tac aag cta tca ctg cgc      192
Tyr Leu Arg Ser Leu Leu His Gln Ala Leu Tyr Lys Leu Ser Leu Arg
    50                  55                  60 tat gga ccc ttg atc cac gtc atg atc ggt tcg aag cac gtg gtg gtg      240
Tyr Gly Pro Leu Ile His Val Met Ile Gly Ser Lys His Val Val Val
65                  70                  75                  80 gcg tcg tcg gcg gag acg gcc aag cag atc ctc aaa acc tcg gag gag      288
Ala Ser Ser Ala Glu Thr Ala Lys Gln Ile Leu Lys Thr Ser Glu Glu
                85                  90                  95 gca ttc tgc aac cgt ccc tta atg ata gcg agc gag agc cta acc tac      336
Ala Phe Cys Asn Arg Pro Leu Met Ile Ala Ser Glu Ser Leu Thr Tyr
            100                 105                 110 ggc gcg gcg gac tac ttc ttc atc ccc tac ggc aca tac tgg cgg ttc      384
Gly Ala Ala Asp Tyr Phe Phe Ile Pro Tyr Gly Thr Tyr Trp Arg Phe
        115                 120                 125 ctg aag aag ctc tgc atg acg gag ctt ctg agc ggg aag acc ctg gag      432
Leu Lys Lys Leu Cys Met Thr Glu Leu Leu Ser Gly Lys Thr Leu Glu
    130                 135                 140 cat ttc gtg aga atc cgc gag agc gag gtg gag gcg ttc ctc aag aga      480
His Phe Val Arg Ile Arg Glu Ser Glu Val Glu Ala Phe Leu Lys Arg
145                 150                 155                 160 atg atg gag att tca ggc aat gga aat tac gag gtg gtg atg agg aag      528
Met Met Glu Ile Ser Gly Asn Gly Asn Tyr Glu Val Val Met Arg Lys
                165                 170                 175 gag ctc ata acg cac acg aat aac atc atc acg agg atg ata atg ggg      576
Glu Leu Ile Thr His Thr Asn Asn Ile Ile Thr Arg Met Ile Met Gly
            180                 185                 190 aag aag agt aat gcg gaa aac gat gag gtg gcc agg ttg agg aag gtg      624
Lys Lys Ser Asn Ala Glu Asn Asp Glu Val Ala Arg Leu Arg Lys Val
        195                 200                 205 gtg agg gag gtc ggg gag ttg ctt ggg gcg ttt aac ttg ggg gat gtt      672
Val Arg Glu Val Gly Glu Leu Leu Gly Ala Phe Asn Leu Gly Asp Val
    210                 215                 220 att ggg ttc atg agg cct ttg gat ctg caa ggg ttt ggg aag aag aac      720
Ile Gly Phe Met Arg Pro Leu Asp Leu Gln Gly Phe Gly Lys Lys Asn
225                 230                 235                 240 atg gaa act cac cac aag gtg gat gcg atg atg gag aag gtg ttg agg      768
Met Glu Thr His His Lys Val Asp Ala Met Met Glu Lys Val Leu Arg
                245                 250                 255 gag cat gag gag gct agg gct aag gaa gat gct gac tct gat agg aag      816
Glu His Glu Glu Ala Arg Ala Lys Glu Asp Ala Asp Ser Asp Arg Lys
            260                 265                 270 aag gat ctt ttt gat att ttg ttg aac ctc att gaa gct gat ggt gct      864
Lys Asp Leu Phe Asp Ile Leu Leu Asn Leu Ile Glu Ala Asp Gly Ala
        275                 280                 285 gac aat aag ctc act aga gag agt gcc aaa gcc ttt gct ctg gac atg      912
Asp Asn Lys Leu Thr Arg Glu Ser Ala Lys Ala Phe Ala Leu Asp Met
```

```
                        290                 295                 300
ttc atc gcc ggc aca aac ggc ccc gca agc gtc cta gag tgg tca ctg      960
Phe Ile Ala Gly Thr Asn Gly Pro Ala Ser Val Leu Glu Trp Ser Leu
305                 310                 315                 320 gcg gag ctg gtg aga aac ccc cac gtt ttc aag aag gca aga gaa gag     1008
Ala Glu Leu Val Arg Asn Pro His Val Phe Lys Lys Ala Arg Glu Glu
                325                 330                 335 att gag tca gtg gta ggc aaa gaa agg ctg gtc aaa gaa tca gac att     1056
Ile Glu Ser Val Val Gly Lys Glu Arg Leu Val Lys Glu Ser Asp Ile
            340                 345                 350 ccc aac cta cca tac cta caa gca ttg ctg aag gaa acc cta agg ctg     1104
Pro Asn Leu Pro Tyr Leu Gln Ala Leu Leu Lys Glu Thr Leu Arg Leu
        355                 360                 365 cac ccg cca acc cca ata ttc gca aga gaa gcc atg cga aca tgc cag     1152
His Pro Pro Thr Pro Ile Phe Ala Arg Glu Ala Met Arg Thr Cys Gln
    370                 375                 380 gtt gaa ggc tac gac att ccg gaa aat tcc act att ttg atc agc aca     1200
Val Glu Gly Tyr Asp Ile Pro Glu Asn Ser Thr Ile Leu Ile Ser Thr
385                 390                 395                 400 tgg gcc att ggt agg gat cca aat tac tgg gat gac gca ctc gag tac     1248
Trp Ala Ile Gly Arg Asp Pro Asn Tyr Trp Asp Asp Ala Leu Glu Tyr
                405                 410                 415 aag ccg gag agg ttc ttg ttc tcc gac gac ccg ggc aag agc aag att     1296
Lys Pro Glu Arg Phe Leu Phe Ser Asp Asp Pro Gly Lys Ser Lys Ile
            420                 425                 430 gac gtg agg ggg cag tac tat cag ctc ctg ccc ttt ggg agc ggg aga     1344
Asp Val Arg Gly Gln Tyr Tyr Gln Leu Leu Pro Phe Gly Ser Gly Arg
        435                 440                 445 aga agc tgc ccc gga gcc tcg cta gcg ttg ctt gtc atg caa gca acg     1392
Arg Ser Cys Pro Gly Ala Ser Leu Ala Leu Leu Val Met Gln Ala Thr
    450                 455                 460 cta gcg agt ttg atc cag tgc ttc gac tgg atc gtt aat gat ggt aaa     1440
Leu Ala Ser Leu Ile Gln Cys Phe Asp Trp Ile Val Asn Asp Gly Lys
465                 470                 475                 480 aac cat cat gtt gac atg tct gag gaa ggg agg gtg act gtg ttt ttg     1488
Asn His His Val Asp Met Ser Glu Glu Gly Arg Val Thr Val Phe Leu
                485                 490                 495 gcc aag cca ctc aag tgc aag cct gtt ccg cgt ttc act ccg ttc gct     1536
Ala Lys Pro Leu Lys Cys Lys Pro Val Pro Arg Phe Thr Pro Phe Ala
            500                 505                 510 gcc tga                                                              1542
Ala

<210> SEQ ID NO 9
<211> LENGTH: 513
<212> TYPE: PRT
<213> ORGANISM: Soybean

<400> SEQUENCE: 9

Met Leu Asp Ile Lys Gly Tyr Leu Val Leu Phe Phe Leu Trp Phe Ile
1               5                   10                  15

Ser Thr Ile Leu Ile Arg Ser Ile Phe Lys Lys Pro Gln Arg Leu Arg
            20                  25                  30

Leu Pro Pro Gly Pro Pro Ile Ser Val Pro Leu Leu Gly His Ala Pro
        35                  40                  45

Tyr Leu Arg Ser Leu Leu His Gln Ala Leu Tyr Lys Leu Ser Leu Arg
    50                  55                  60

Tyr Gly Pro Leu Ile His Val Met Ile Gly Ser Lys His Val Val Val
65                  70                  75                  80
```

-continued

```
Ala Ser Ser Ala Glu Thr Ala Lys Gln Ile Leu Lys Thr Ser Glu Glu
                85                  90                  95

Ala Phe Cys Asn Arg Pro Leu Met Ile Ala Ser Glu Ser Leu Thr Tyr
            100                 105                 110

Gly Ala Ala Asp Tyr Phe Phe Ile Pro Tyr Gly Thr Tyr Trp Arg Phe
        115                 120                 125

Leu Lys Lys Leu Cys Met Thr Glu Leu Ser Gly Lys Thr Leu Glu
    130                 135                 140

His Phe Val Arg Ile Arg Glu Ser Glu Val Glu Ala Phe Leu Lys Arg
145                 150                 155                 160

Met Met Glu Ile Ser Gly Asn Gly Asn Tyr Glu Val Val Met Arg Lys
                165                 170                 175

Glu Leu Ile Thr His Thr Asn Asn Ile Thr Arg Met Ile Met Gly
            180                 185                 190

Lys Lys Ser Asn Ala Glu Asn Asp Glu Val Ala Arg Leu Arg Lys Val
        195                 200                 205

Val Arg Glu Val Gly Glu Leu Leu Gly Ala Phe Asn Leu Gly Asp Val
    210                 215                 220

Ile Gly Phe Met Arg Pro Leu Asp Leu Gln Gly Phe Gly Lys Lys Asn
225                 230                 235                 240

Met Glu Thr His His Lys Val Asp Ala Met Met Glu Lys Val Leu Arg
                245                 250                 255

Glu His Glu Glu Ala Arg Ala Lys Glu Asp Ala Asp Ser Asp Arg Lys
            260                 265                 270

Lys Asp Leu Phe Asp Ile Leu Leu Asn Leu Ile Glu Ala Asp Gly Ala
        275                 280                 285

Asp Asn Lys Leu Thr Arg Glu Ser Ala Lys Ala Phe Ala Leu Asp Met
    290                 295                 300

Phe Ile Ala Gly Thr Asn Gly Pro Ala Ser Val Leu Glu Trp Ser Leu
305                 310                 315                 320

Ala Glu Leu Val Arg Asn Pro His Val Phe Lys Lys Ala Arg Glu Glu
                325                 330                 335

Ile Glu Ser Val Val Gly Lys Glu Arg Leu Val Lys Glu Ser Asp Ile
            340                 345                 350

Pro Asn Leu Pro Tyr Leu Gln Ala Leu Leu Lys Glu Thr Leu Arg Leu
        355                 360                 365

His Pro Pro Thr Pro Ile Phe Ala Arg Glu Ala Met Arg Thr Cys Gln
    370                 375                 380

Val Glu Gly Tyr Asp Ile Pro Glu Asn Ser Thr Ile Leu Ile Ser Thr
385                 390                 395                 400

Trp Ala Ile Gly Arg Asp Pro Asn Tyr Trp Asp Ala Leu Glu Tyr
                405                 410                 415

Lys Pro Glu Arg Phe Leu Phe Ser Asp Asp Pro Gly Lys Ser Lys Ile
            420                 425                 430

Asp Val Arg Gly Gln Tyr Tyr Gln Leu Leu Pro Phe Gly Ser Gly Arg
        435                 440                 445

Arg Ser Cys Pro Gly Ala Ser Leu Ala Leu Leu Val Met Gln Ala Thr
    450                 455                 460

Leu Ala Ser Leu Ile Gln Cys Phe Asp Trp Ile Val Asn Asp Gly Lys
465                 470                 475                 480

Asn His His Val Asp Met Ser Glu Glu Gly Arg Val Thr Val Phe Leu
                485                 490                 495
```

```
Ala Lys Pro Leu Lys Cys Lys Pro Val Pro Arg Phe Thr Pro Phe Ala
            500                 505                 510
Ala

<210> SEQ ID NO 10
<211> LENGTH: 1542
<212> TYPE: DNA
<213> ORGANISM: Soybean
<220> FEATURE:
<221> NAME/KEY: CDS
<222> LOCATION: (1)..(1542)

<400> SEQUENCE: 10 atg cta gac atc aaa ggc tac ctc gta ctc ttc ttc cta tgg ttc ata      48
Met Leu Asp Ile Lys Gly Tyr Leu Val Leu Phe Phe Leu Trp Phe Ile
1               5                   10                  15 tca acc att ctg ata cgt tcc atc ttc aag aaa cca cag cgt cta aga      96
Ser Thr Ile Leu Ile Arg Ser Ile Phe Lys Lys Pro Gln Arg Leu Arg
                20                  25                  30 ctc cca ccg ggt cct cca att tca ata ccc ttg ctg gga cac gcg cca     144
Leu Pro Pro Gly Pro Pro Ile Ser Ile Pro Leu Leu Gly His Ala Pro
            35                  40                  45 tat ctc cgt tca ctg ctc cac caa gca ttg tac aag cta tca ctg cgc     192
Tyr Leu Arg Ser Leu Leu His Gln Ala Leu Tyr Lys Leu Ser Leu Arg
        50                  55                  60 tat gga ccc ttg atc cac gtc atg atc ggt tcg aag cac gtg gtg gtg     240
Tyr Gly Pro Leu Ile His Val Met Ile Gly Ser Lys His Val Val Val
65                  70                  75                  80 gcg tcg tcg gcg gag acg gcc aag cag atc ctc aaa acc tcg gag gag     288
Ala Ser Ser Ala Glu Thr Ala Lys Gln Ile Leu Lys Thr Ser Glu Glu
                85                  90                  95 gca ttc tgc aac cgt ccc tta atg ata gcg agc gag agc cta acc tac     336
Ala Phe Cys Asn Arg Pro Leu Met Ile Ala Ser Glu Ser Leu Thr Tyr
            100                 105                 110 ggc gcg gcg gac tac ttc ttc atc ccc tac ggc aca tac tgg cgg ttc     384
Gly Ala Ala Asp Tyr Phe Phe Ile Pro Tyr Gly Thr Tyr Trp Arg Phe
        115                 120                 125 ctg aag aag ctc tgc atg acg gag ctt ctg agc ggg aag acc ctg gag     432
Leu Lys Lys Leu Cys Met Thr Glu Leu Leu Ser Gly Lys Thr Leu Glu
    130                 135                 140 cat ttc gtg aga atc cgc gag agc gag gtg gag gcg ttc ctc aag aga     480
His Phe Val Arg Ile Arg Glu Ser Glu Val Glu Ala Phe Leu Lys Arg
145                 150                 155                 160 atg atg gag att tca ggc aat gga aat tac gag gtg gtg atg agg aag     528
Met Met Glu Ile Ser Gly Asn Gly Asn Tyr Glu Val Val Met Arg Lys
                165                 170                 175 gag ctc ata acg cac acg aat aac atc atc acg agg atg ata atg ggg     576
Glu Leu Ile Thr His Thr Asn Asn Ile Ile Thr Arg Met Ile Met Gly
            180                 185                 190 aag aag agt aat gcg gaa aac gat gag gtg gcc agg ttg agg aag gtg     624
Lys Lys Ser Asn Ala Glu Asn Asp Glu Val Ala Arg Leu Arg Lys Val
        195                 200                 205 gtg agg gag gtc ggg gag ttg ctt ggg gcg ttt aac ttg ggg gat gtt     672
Val Arg Glu Val Gly Glu Leu Leu Gly Ala Phe Asn Leu Gly Asp Val
    210                 215                 220 att ggg ttc atg agg cct ttg gat ctg caa ggg ttt ggg aag aag aac     720
Ile Gly Phe Met Arg Pro Leu Asp Leu Gln Gly Phe Gly Lys Lys Asn
225                 230                 235                 240 atg gaa act cac cac aag gtg gat gcg atg atg gag aag gtg ttg agg     768
Met Glu Thr His His Lys Val Asp Ala Met Met Glu Lys Val Leu Arg
                245                 250                 255
```

| | | | | | | | | | | | | | | | | |
|---|---|---|---|---|---|---|---|---|---|---|---|---|---|---|---|---|
| gag | cat | gag | gag | gct | agg | gct | aag | gaa | gat | gct | gac | tct | gat | agg | aag | 816 |
| Glu | His | Glu | Glu | Ala | Arg | Ala | Lys | Glu | Asp | Ala | Asp | Ser | Asp | Arg | Lys | |
| | | 260 | | | | | 265 | | | | | 270 | | | | |
| aag | gat | ctt | ttt | gat | att | ttg | ttg | aac | ctc | att | gaa | gct | gat | ggt | gct | 864 |
| Lys | Asp | Leu | Phe | Asp | Ile | Leu | Leu | Asn | Leu | Ile | Glu | Ala | Asp | Gly | Ala | |
| | | | 275 | | | | | 280 | | | | | 285 | | | |
| gac | aat | aag | ctc | act | aga | gag | agt | gcc | aaa | gcc | ttt | gct | ctg | gac | atg | 912 |
| Asp | Asn | Lys | Leu | Thr | Arg | Glu | Ser | Ala | Lys | Ala | Phe | Ala | Leu | Asp | Met | |
| | | 290 | | | | | 295 | | | | | 300 | | | | |
| ttc | atc | gcc | ggc | aca | aac | ggc | ccc | gca | agc | gtc | cta | gag | tgg | tca | ctg | 960 |
| Phe | Ile | Ala | Gly | Thr | Asn | Gly | Pro | Ala | Ser | Val | Leu | Glu | Trp | Ser | Leu | |
| 305 | | | | | 310 | | | | | 315 | | | | | 320 | |
| gcg | gag | ctg | gtg | aga | aac | ccc | cac | gtt | ttc | aag | aag | gca | aga | gaa | gag | 1008 |
| Ala | Glu | Leu | Val | Arg | Asn | Pro | His | Val | Phe | Lys | Lys | Ala | Arg | Glu | Glu | |
| | | | | 325 | | | | | 330 | | | | | 335 | | |
| att | gag | tca | gtg | gta | ggc | aaa | gaa | agg | ctg | gtc | aaa | gaa | tca | gac | att | 1056 |
| Ile | Glu | Ser | Val | Val | Gly | Lys | Glu | Arg | Leu | Val | Lys | Glu | Ser | Asp | Ile | |
| | | | 340 | | | | | 345 | | | | | 350 | | | |
| ccc | aac | cta | cca | tac | cta | caa | gca | gtg | ctg | aag | gaa | acc | cta | agg | ctg | 1104 |
| Pro | Asn | Leu | Pro | Tyr | Leu | Gln | Ala | Val | Leu | Lys | Glu | Thr | Leu | Arg | Leu | |
| | | 355 | | | | | 360 | | | | | 365 | | | | |
| cac | ccg | cca | acc | cca | ata | ttc | gca | aga | gaa | gcc | atg | cga | aca | tgc | cag | 1152 |
| His | Pro | Pro | Thr | Pro | Ile | Phe | Ala | Arg | Glu | Ala | Met | Arg | Thr | Cys | Gln | |
| | 370 | | | | | 375 | | | | | 380 | | | | | |
| gtt | gaa | ggc | tac | gac | att | ccg | gaa | aat | tcc | act | att | ttg | atc | agc | aca | 1200 |
| Val | Glu | Gly | Tyr | Asp | Ile | Pro | Glu | Asn | Ser | Thr | Ile | Leu | Ile | Ser | Thr | |
| 385 | | | | | 390 | | | | | 395 | | | | | 400 | |
| tgg | gcc | att | ggt | agg | gat | cca | aat | tac | tgg | gat | gac | gca | ctc | gag | tac | 1248 |
| Trp | Ala | Ile | Gly | Arg | Asp | Pro | Asn | Tyr | Trp | Asp | Asp | Ala | Leu | Glu | Tyr | |
| | | | | 405 | | | | | 410 | | | | | 415 | | |
| aag | ccg | gag | agg | ttc | ttg | ttc | tcc | gac | gac | ccg | ggc | aag | agc | aag | att | 1296 |
| Lys | Pro | Glu | Arg | Phe | Leu | Phe | Ser | Asp | Asp | Pro | Gly | Lys | Ser | Lys | Ile | |
| | | | 420 | | | | | 425 | | | | | 430 | | | |
| gac | gtg | agg | ggg | cag | tac | tat | cag | ctc | ctg | ccc | ttt | ggg | agc | ggg | aga | 1344 |
| Asp | Val | Arg | Gly | Gln | Tyr | Tyr | Gln | Leu | Leu | Pro | Phe | Gly | Ser | Gly | Arg | |
| | | 435 | | | | | 440 | | | | | 445 | | | | |
| aga | agc | tgc | ccc | gga | gcc | tcg | cta | gcg | ttg | ctt | gtc | atg | caa | gca | acg | 1392 |
| Arg | Ser | Cys | Pro | Gly | Ala | Ser | Leu | Ala | Leu | Leu | Val | Met | Gln | Ala | Thr | |
| | 450 | | | | | 455 | | | | | 460 | | | | | |
| cta | gcg | agt | ttg | atc | cag | tgc | ttc | gac | tgg | atc | gtt | aat | gat | ggt | aaa | 1440 |
| Leu | Ala | Ser | Leu | Ile | Gln | Cys | Phe | Asp | Trp | Ile | Val | Asn | Asp | Gly | Lys | |
| 465 | | | | | 470 | | | | | 475 | | | | | 480 | |
| aac | cat | cat | gtt | gac | atg | tct | gag | gaa | ggg | agg | gtg | act | gtg | ttt | ttg | 1488 |
| Asn | His | His | Val | Asp | Met | Ser | Glu | Glu | Gly | Arg | Val | Thr | Val | Phe | Leu | |
| | | | | 485 | | | | | 490 | | | | | 495 | | |
| gcc | aag | cca | ctc | aag | tgc | aag | cct | gtt | ccg | cgt | ttc | act | ccg | ttc | gct | 1536 |
| Ala | Lys | Pro | Leu | Lys | Cys | Lys | Pro | Val | Pro | Arg | Phe | Thr | Pro | Phe | Ala | |
| | | | 500 | | | | | 505 | | | | | 510 | | | |
| gcc | tga | | | | | | | | | | | | | | | 1542 |
| Ala | | | | | | | | | | | | | | | | |

<210> SEQ ID NO 11
<211> LENGTH: 513
<212> TYPE: PRT
<213> ORGANISM: Soybean

<400> SEQUENCE: 11

Met Leu Asp Ile Lys Gly Tyr Leu Val Leu Phe Phe Leu Trp Phe Ile
1               5                   10                  15

-continued

```
Ser Thr Ile Leu Ile Arg Ser Ile Phe Lys Lys Pro Gln Arg Leu Arg
         20                  25                  30

Leu Pro Pro Gly Pro Pro Ile Ser Ile Pro Leu Leu Gly His Ala Pro
         35                  40                  45

Tyr Leu Arg Ser Leu Leu His Gln Ala Leu Tyr Lys Leu Ser Leu Arg
50                       55                  60

Tyr Gly Pro Leu Ile His Val Met Ile Gly Ser Lys His Val Val
65                  70                  75                  80

Ala Ser Ser Ala Glu Thr Ala Lys Gln Ile Leu Lys Thr Ser Glu Glu
                 85                  90                  95

Ala Phe Cys Asn Arg Pro Leu Met Ile Ala Ser Glu Ser Leu Thr Tyr
                 100                 105                 110

Gly Ala Ala Asp Tyr Phe Phe Ile Pro Tyr Gly Thr Tyr Trp Arg Phe
                 115                 120                 125

Leu Lys Lys Leu Cys Met Thr Glu Leu Leu Ser Gly Lys Thr Leu Glu
        130                 135                 140

His Phe Val Arg Ile Arg Glu Ser Glu Val Glu Ala Phe Leu Lys Arg
145                 150                 155                 160

Met Met Glu Ile Ser Gly Asn Gly Asn Tyr Glu Val Val Met Arg Lys
                 165                 170                 175

Glu Leu Ile Thr His Thr Asn Asn Ile Ile Thr Arg Met Ile Met Gly
                 180                 185                 190

Lys Lys Ser Asn Ala Glu Asn Asp Glu Val Ala Arg Leu Arg Lys Val
        195                 200                 205

Val Arg Glu Val Gly Glu Leu Leu Gly Ala Phe Asn Leu Gly Asp Val
        210                 215                 220

Ile Gly Phe Met Arg Pro Leu Asp Leu Gln Gly Phe Gly Lys Lys Asn
225                 230                 235                 240

Met Glu Thr His His Lys Val Asp Ala Met Met Glu Lys Val Leu Arg
                 245                 250                 255

Glu His Glu Glu Ala Arg Ala Lys Glu Asp Ala Asp Ser Asp Arg Lys
                 260                 265                 270

Lys Asp Leu Phe Asp Ile Leu Leu Asn Leu Ile Glu Ala Asp Gly Ala
        275                 280                 285

Asp Asn Lys Leu Thr Arg Glu Ser Ala Lys Ala Phe Ala Leu Asp Met
        290                 295                 300

Phe Ile Ala Gly Thr Asn Gly Pro Ala Ser Val Leu Glu Trp Ser Leu
305                 310                 315                 320

Ala Glu Leu Val Arg Asn Pro His Val Phe Lys Ala Arg Glu Glu
                 325                 330                 335

Ile Glu Ser Val Val Gly Lys Glu Arg Leu Val Lys Ser Asp Ile
                 340                 345                 350

Pro Asn Leu Pro Tyr Leu Gln Ala Val Leu Lys Glu Thr Leu Arg Leu
        355                 360                 365

His Pro Pro Thr Pro Ile Phe Ala Arg Glu Ala Met Arg Thr Cys Gln
        370                 375                 380

Val Glu Gly Tyr Asp Ile Pro Glu Asn Ser Thr Ile Leu Ile Ser Thr
385                 390                 395                 400

Trp Ala Ile Gly Arg Asp Pro Asn Tyr Trp Asp Asp Ala Leu Glu Tyr
                 405                 410                 415

Lys Pro Glu Arg Phe Leu Phe Ser Asp Asp Pro Gly Lys Ser Lys Ile
                 420                 425                 430

Asp Val Arg Gly Gln Tyr Tyr Gln Leu Leu Pro Phe Gly Ser Gly Arg
```

```
                    435                 440                 445
Arg Ser Cys Pro Gly Ala Ser Leu Ala Leu Leu Val Met Gln Ala Thr
        450                 455                 460

Leu Ala Ser Leu Ile Gln Cys Phe Asp Trp Ile Val Asn Asp Gly Lys
465                 470                 475                 480

Asn His His Val Asp Met Ser Glu Glu Gly Arg Val Thr Val Phe Leu
                485                 490                 495

Ala Lys Pro Leu Lys Cys Lys Pro Val Pro Arg Phe Thr Pro Phe Ala
            500                 505                 510

Ala
```

The invention claimed is:

1. An isolated expression vector comprising a polynucleotide encoding the polypeptide of SEQ ID NO:9, wherein the polypeptide of SEQ ID NO:9 hydroxylates the 24-position of an oleanane-type triterpene.

2. The expression vector described in claim 1, wherein the polynucleotide is the polynucleotide of SEQ ID NO:8.

3. A microorganism transformed with the expression vector of claim 1.

4. The microorganism of claim 3, wherein the microorganism is a yeast.

5. An isolated co-expression vector comprising a polynucleotide encoding the polypeptide of SEQ ID NO:9 and a β-amyrin synthase gene.

6. The expression vector described in claim 5, wherein the polynucleotide is the polynucleotide of SEQ ID NO:8.

7. A microorganism transformed with the expression vector of claim 5.

8. The microorganism of claim 7, wherein the microorganism is a yeast.

9. A lanosterol synthase deficient yeast mutant strain deposited as FERM BP-10201.

10. A method for producing a polypeptide that hydroxylates the 24-position of an oleanane type triterpene comprising culturing the microorganism described in claim 3 to produce the polypeptide of SEQ ID NO:9.

11. A method for producing a polypeptide that hydroxylates the 24-position of an oleanane type triterpene and a β-amyrin synthase, comprising culturing the microorganism described in claim 7 to produce the polypeptide of SEQ ID NO:9 and a β-amyrin synthase.

12. A method for hydroxylating the 24-position of an oleanane-type triterpene, comprising culturing the microorganism of claim 3 in the presence of an oleanane-type triterpene, thereby hydroxylating the 24-position of the oleanane-type triterpene.

13. A method for hydroxylating the 24-position of an oleanane-type triterpene, comprising culturing the microorganism of claim 7 in the presence of an oleanane-type triterpene, thereby hydroxylating the 24-position of the oleanane-type triterpene.

14. A method for hydroxylating the 24-position of an oleanane-type triterpene, comprising culturing the yeast mutant strain of claim 9 in the presence of an oleanane-type triterpene, thereby hydroxylating the 24-position of the oleanane-type triterpene.

* * * * *